United States Patent
John

(10) Patent No.: US 8,965,509 B2
(45) Date of Patent: Feb. 24, 2015

(54) METHODS AND SYSTEMS FOR SEMI-AUTOMATIC ADJUSTMENT OF MEDICAL MONITORING AND TREATMENT

(76) Inventor: Michael Sasha John, Larchmont, NY (US)

( * ) Notice: Subject to any disclaimer, the term of this patent is extended or adjusted under 35 U.S.C. 154(b) by 779 days.

(21) Appl. No.: 11/932,955

(22) Filed: Oct. 31, 2007

(65) Prior Publication Data

US 2008/0071314 A1 Mar. 20, 2008

Related U.S. Application Data

(63) Continuation of application No. 11/877,897, filed on Oct. 24, 2007, which is a continuation-in-part of application No. 11/309,605, filed on Aug. 30, 2006.

(60) Provisional application No. 60/862,799, filed on Oct. 25, 2006, provisional application No. 60/596,095, filed on Aug. 31, 2005, provisional application No. 60/596,693, filed on Oct. 13, 2005.

(51) Int. Cl.
*A61N 1/00* (2006.01)
*A61N 1/372* (2006.01)
*A61B 5/00* (2006.01)

(52) U.S. Cl.
CPC .......... *A61N 1/37247* (2013.01); *A61B 5/4809* (2013.01); *A61N 1/37258* (2013.01); *A61B 5/00* (2013.01); *A61B 5/4812* (2013.01); *A61B 5/4818* (2013.01)
USPC .......................................................... 607/32

(58) Field of Classification Search
USPC ........... 600/300, 347, 508; 607/17, 30, 48, 59
See application file for complete search history.

(56) References Cited

U.S. PATENT DOCUMENTS

| | | | |
|---|---|---|---|
| 5,716,377 A | 2/1998 | Rise | 607/2 |
| 6,234,964 B1 * | 5/2001 | Iliff | 600/300 |
| 6,246,992 B1 | 6/2001 | Brown | 705/2 |
| 6,269,340 B1 | 7/2001 | Ford | 604/891.1 |
| 6,308,102 B1 | 10/2001 | Sieracki | 607/59 |
| 6,463,328 B1 | 10/2002 | John | 607/45 |
| 6,551,276 B1 | 4/2003 | Mann | 604/131 |
| 6,558,321 B1 * | 5/2003 | Burd et al. | 600/300 |
| 6,748,260 B2 | 6/2004 | Au | 600/509 |
| 6,782,292 B2 | 8/2004 | Whitehurst | 607/45 |
| 6,832,114 B1 | 12/2004 | Whitehurst | 607/40 |
| 6,871,098 B2 | 3/2005 | Nuttin | 607/45 |
| 6,880,564 B2 | 4/2005 | Erickson | 137/1 |
| 6,923,784 B2 | 8/2005 | Stein | 604/67 |
| 6,986,347 B2 | 1/2006 | Hickle | 128/200.24 |

(Continued)

*Primary Examiner* — Luther Behringer
(74) *Attorney, Agent, or Firm* — Rosenberg, Klein & Lee

(57) ABSTRACT

Systems and methods are described for adjusting the operation of implantable stimulation devices used to provide medical monitoring and treatment. Several hierarchical algorithms are described which operate according to conditionally obtaining a patient response to an alert signal. In one such strategy semi-automatic therapy adjustment occurs by automatically issuing patient alert messages when selected operations are to occur, and using a patient's response to the alert message that is provided within a selected time limit in order to contingently adjust therapy. Methods are also described for resolving conflicts which may occur when time information and sensed data information each indicate different patient states are occurring. Although treatment of neural and cardiac disorders is emphasized, the techniques can be applied to the monitoring and treatment of any medical disorder with an implanted device.

25 Claims, 12 Drawing Sheets

(56) References Cited

U.S. PATENT DOCUMENTS

| | | | |
|---|---|---|---|
| 6,999,854 B2 | 2/2006 | Roth | 700/282 |
| 7,008,413 B2 | 3/2006 | Kovach | 604/891.1 |
| 7,025,743 B2 | 4/2006 | Mann | 604/45 |
| 7,035,690 B2 | 4/2006 | Goetz | 607/46 |
| 7,406,349 B2 * | 7/2008 | Seeberger et al. | 607/30 |
| 2001/0007950 A1 * | 7/2001 | North et al. | 607/59 |
| 2002/0026223 A1 | 2/2002 | Riff | 607/27 |
| 2002/0038137 A1 | 3/2002 | Stein | 607/46 |
| 2002/0052539 A1 * | 5/2002 | Haller et al. | 600/300 |
| 2002/0065453 A1 * | 5/2002 | Lesho et al. | 600/347 |
| 2002/0087116 A1 | 7/2002 | Hartlaub | 604/65 |
| 2002/0099302 A1 | 7/2002 | Bardy | 600/510 |
| 2003/0135087 A1 | 7/2003 | Hickle | 128/204.18 |
| 2003/0145854 A1 | 8/2003 | Hickle | 128/204.18 |
| 2004/0122297 A1 * | 6/2004 | Stahmann et al. | 600/300 |
| 2004/0138716 A1 * | 7/2004 | Kon et al. | 607/17 |
| 2004/0181262 A1 * | 9/2004 | Bauhahn | 607/48 |
| 2004/0199215 A1 | 10/2004 | Lee | 607/48 |
| 2004/0215286 A1 | 10/2004 | Stypulkowski | 607/48 |
| 2005/0081847 A1 | 4/2005 | Lee | 128/200.24 |
| 2005/0137483 A1 | 6/2005 | Fischell | 600/509 |
| 2005/0165321 A1 | 7/2005 | Fischell | 600/515 |
| 2005/0215914 A1 * | 9/2005 | Bornzin et al. | 600/508 |
| 2005/0241026 A1 | 10/2005 | Esler | 705/2 |
| 2005/0277912 A1 | 12/2005 | John | 604/890.1 |
| 2006/0173406 A1 | 8/2006 | Hayes | 604/67 |

* cited by examiner

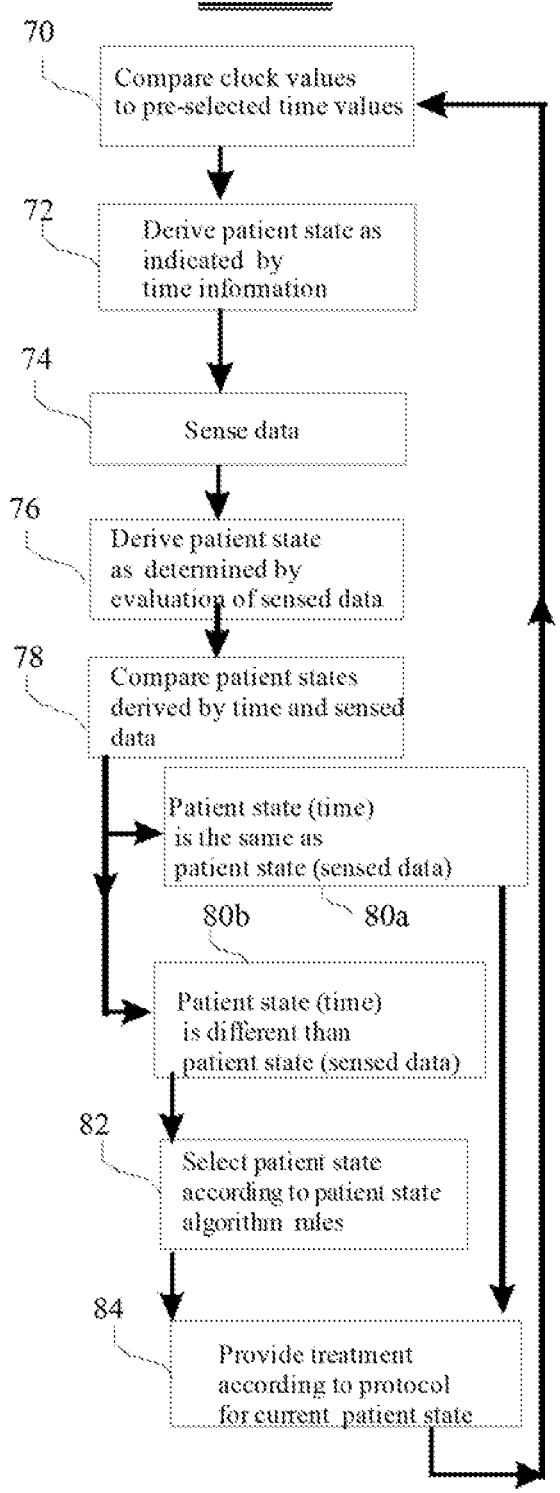

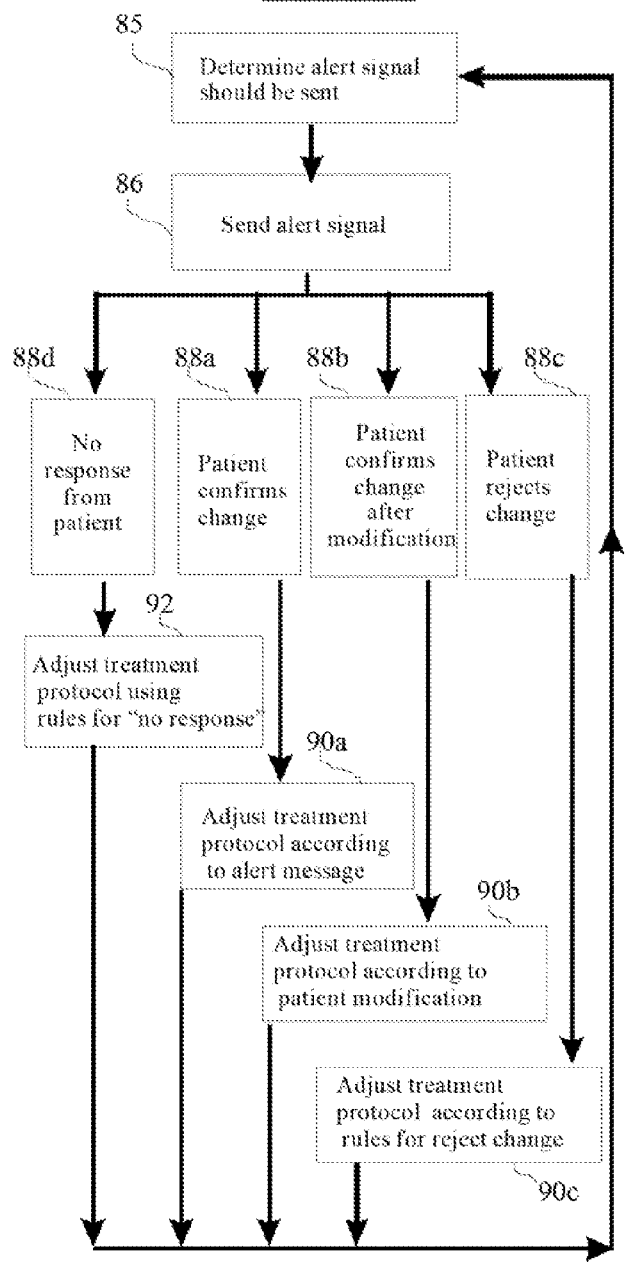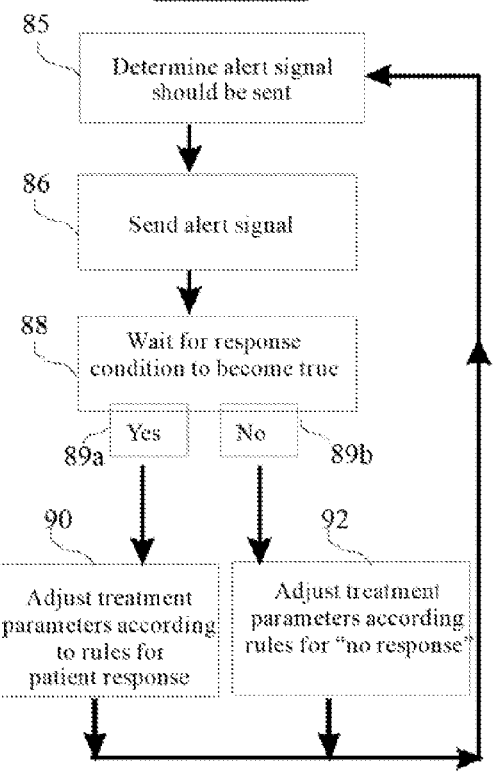

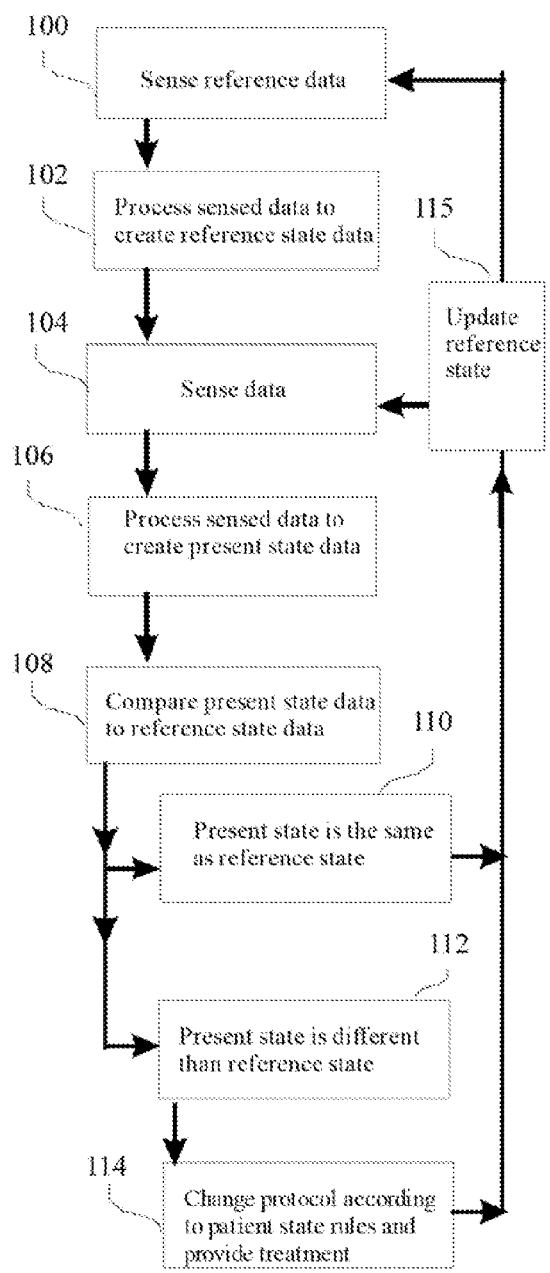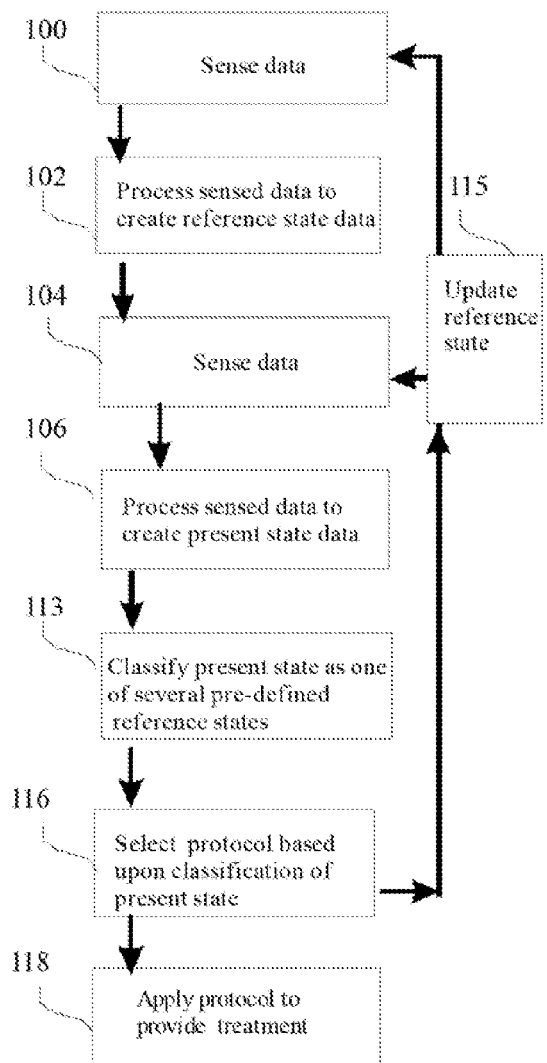

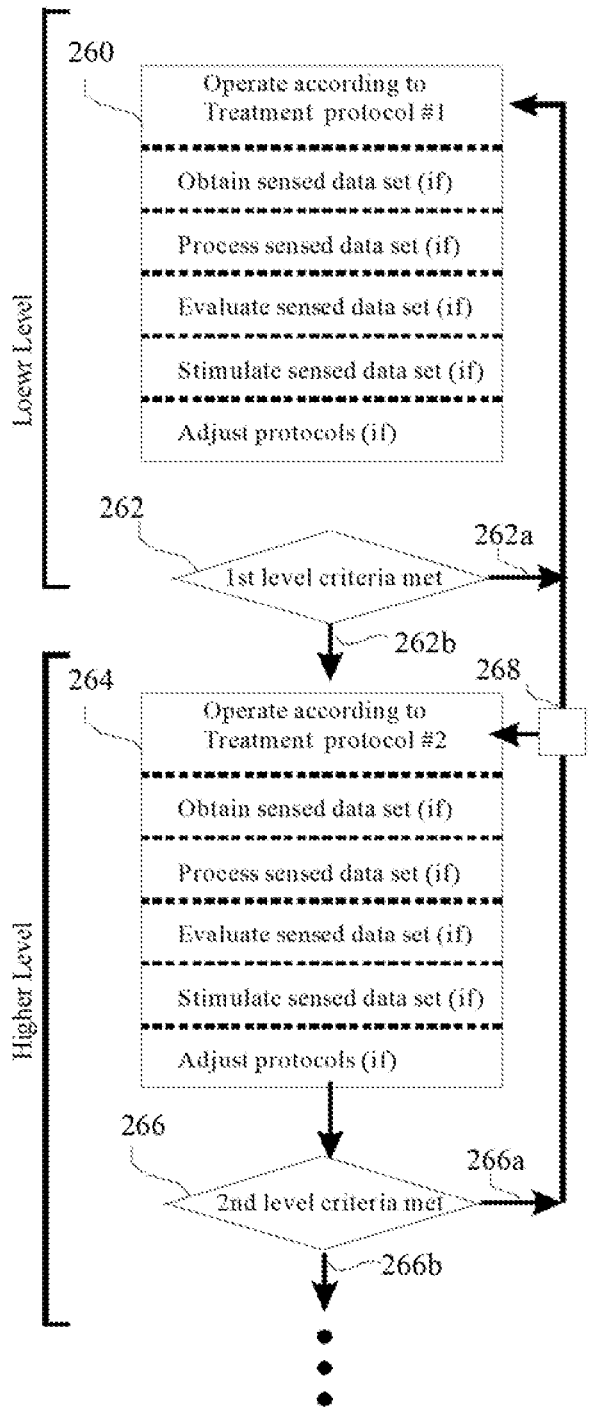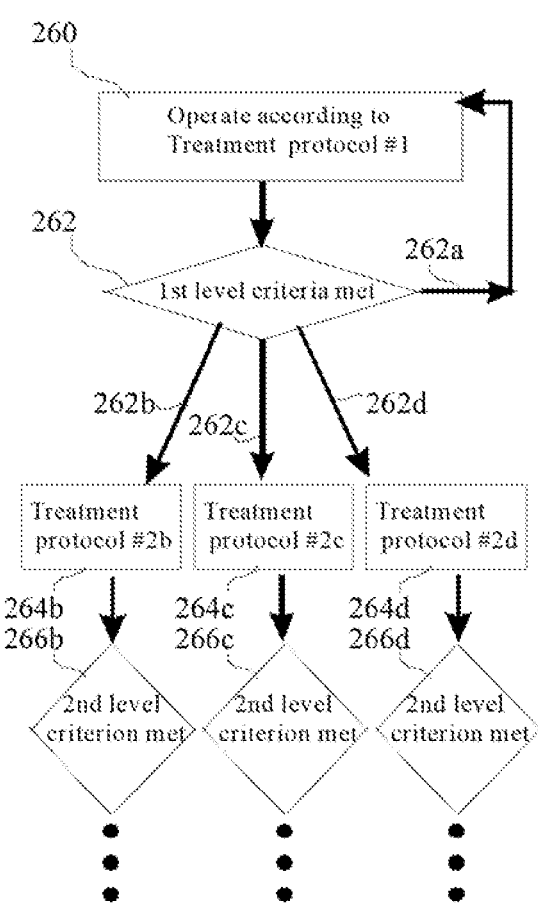
FIG 10A
FIG 10B

METHODS AND SYSTEMS FOR SEMI-AUTOMATIC ADJUSTMENT OF MEDICAL MONITORING AND TREATMENT

CROSS REFERENCE TO RELATED APPLICATIONS

This application is a continuation of U.S. application Ser. No. 11/877,897, filed Oct. 24, 2007, entitled "Methods and Systems for semi-automatic adjustment of medical monitoring and treatment" which is a continuation-in-part of U.S. patent application U.S. application Ser. No. 11/309,605 filed Aug. 30, 2006, entitled "Medical treatment using patient states, patient alerts, and hierarchical algorithm", said application claiming priority of U.S. Provisional application No. 60/862,799 filed Oct. 25, 2006, entitled "Medical treatment using patient states, patient alerts, and hierarchical algorithms" and U.S. Provisional application No. 60/596,095 filed, Aug. 31, 2005, entitled "Therapeutic treatment of medical disorders based on timing and state information" and U.S. Provisional application No. 60/596,693 filed Oct. 13, 2005, entitled "Systems and Methods for Tissue Stimulation in Medical Treatment;"

FIELD

This invention is in the field of implantable monitoring and stimulation devices, and more particularly to systems and methods of providing or adjusting treatment based upon patient preference, patient state values, and patient response values obtained from user input.

BACKGROUND

Medical stimulation devices that provide electrical and drug therapy are being used to treat a growing number of medical disorders. One type of stimulation device is an implantable pulse generator (IPG), which may be programmable and can provide stimulation according to a set of customized stimulation protocols. These protocols are tailored, and sometimes automatically and continuously adjusted, according to a patient's needs. An IPG is usually coupled to an electrical lead containing electrical contacts that provide stimulation to target tissue. When the IPG serves as a neurostimulator, the lead is typically implanted to stimulate a particular region in the brain, vagus nerve, or spinal cord of a patient. The energy delivered through the leads'contacts creates electrical fields that modulates nearly tissue to produce excitation, inhibition, or other modulation (e.g., promoting firing at a particular frequency or according to a pattern) intended to provide treatment for the disorder and relief from its symptoms. Another type of stimulation device is a drug delivery system in which a catheter is normally coupled to a pump that transmits drug from an implanted reservoir to targets that are in, or near, a treatment site.

Implantable stimulation devices can responsively provide treatment in accordance with the patient's needs. For example, a sensor can obtain sensed data related to the activity or chemical level in adjacent tissue, and the sensed data can then be processed to extract features. These features are then evaluated in relation to treatment criteria, and trigger stimulation treatment in response to defined medically relevant events when these are detected. Sensed activity can also be used to automatically adjust the stimulation protocol according to the features of the detected events or the patient's state. Sensed activity may also be used to responsively provide and adjust a stimulation signal according to features of the sensed signal using methods such as control laws. For example, in the treatment of movement disorders, stimulation can be automatically increased in response to sensed data which indicate increased tremor activity using a proportional control law. U.S. Pat. Nos. 7,008,413, 6,463,328, 6,871,098, 6,832,114, 6,782,292, and 5,716,377, and a wide array of other patents disclose various methods of treating medical disorders (e.g., neurological, psychiatric, endocrine, metabolic, pain, cardiac, and movement disorders) by closed-loop stimulation treatment where adjustment and provision of stimulation can occur automatically. In practice, fully automatic methods of providing stimulation may perform an intended to greater or lesser extents due to individual differences of the patient and the variability of the patient's daily routine. Many stimulation systems also allow patients to adjust treatment protocols using an external patient programmer that communicates with the implanted device. Even when automatic programs are used, patients can invoke, adjust or cancel stimulation characteristics set and used automatically by the device to improve therapy in accordance with their preferences.

Implanted devices are normally powered by an implantable power source such as a battery that may be rechargeable or replaceable. In the case of both rechargeable and replaceable batteries, power usage is an important issue. Considerable benefit is obtained by decreasing power consumption and the need for replacement of electrical energy and, in the case of drug delivery systems, medication. Many known systems and methods provide therapy regardless of the time of day, or the activity level or state of the patient. During periods of sleep, phenomena associated with disorders (e.g. tremor and movement disorders) may be absent, greatly diminished, or may simply not require treatment since these do not have any negative impact on the patient. Stimulating identically during sleep and awake states is not an efficient use of resources and requires more frequent replenishment of the power or drug supply. One class of stimulators does not have sensing capabilities and thus does not change stimulation based upon changes sensed in the patient. Even when the stimulation system does not have a sensor, stimulation may be turned off and on by the patient in relation to periods of sleep. Time information can be used to automatically infer patient state and adjust stimulation accordingly.

The more recent generation of implantable stimulation devices is becoming increasingly capable of automatically and responsively providing stimulation according to the detection and quantification of unwanted medical events such as seizures. This will increase battery life and decrease habituation to stimulation since stimulation occurs as needed in response to detected events rather than more or less continuously. Even in stimulators that have sensing capability, patient state may often be ignored. More specifically, these systems provide for adjusting the stimulation protocol in response to sensed data (e.g., detection and quantification of medically relevant events), regardless of certain other factors that should also be considered such as patient state (e.g. the arousal level of a patient which is not related to medically relevant events). Unless the patient manually turns off the stimulator, stimulation often occurs regardless of whether the patient is awake or asleep.

Aside from unnecessarily depleting resources, a second and possibly more important factor is that, in some disorders, providing continuous stimulation generally increases the risk that a patient will develop tolerance, and subsequently need increased stimulation to achieve the same level of treatment benefit. In order to mitigate these two concerns, patients will often be instructed to manually turn off a stimulation device, such as a neurostimulator, at night or while sleeping. However, patients may occasionally or even regularly forget to follow these instructions and, even when they do remember, the return of symptoms prior to falling asleep may inhibit the patient from subsequently achieving sleep. The use of stimulators, which automatically adjust the stimulation treatment according to the patient's daily routines (e.g., as can be indicated by pre-defined times or sensed data), will improve treatment in these cases.

Three known approaches have provided methods of automatically altering treatment according to time information or sensed data. In U.S. Pat. No. 6,463,328 to John ("the '328 patent"), multiple stimulation leads or drugs may be used to treat neurological disorders. The stimulation protocol that governs therapy provided at each stimulation conduit can be governed by "conditional criteria". As described in the '328 patent. "Conditional criteria are additional parameters such as time since last stimulation, time of day, etc., and can be designed so that stimulation occurs only at certain stimulators under specified conditions" Accordingly, stimulation occurs only during certain times, for example, while the patient is normally awake.

It is instructive to note that the '328 patent also describes that even in cases of coma "stimulation can be set to reinforce present or emerging circadian cycles and not to occur during an inappropriate chrono-biological state, such as periods which might suggest sleep or less active states". In this patent, if sensed data indicate that the patient is sleeping, or if conditional criteria indicate that stimulation should not occur during a specific time of day (for example, when the patient is likely to be sleeping) then stimulation does not occur. In the '328 patent the changes occur automatically according to sensed data or time information. The patient is not alerted to, or questioned about, the changes made by the device, nor are adjustments other than "on" vs. "off" specifically addressed.

More recently, U.S. Pat. No. 6,923,784 to Stein ("the '784 patent") describes "automatically shutting off the electrical stimulation or drug delivery during periods when the patient does not require treatment therapy." Stimulation is halted when sleep is detected or during times when sleep is likely. While much of the '784 patent appears to describe methods already taught and claimed in the '328 patent, two features are worth noting. Conflicts between sensor readings and the time of day criteria are resolved automatically and without patient intervention. In one example, if the time of day indicates that stimulation should be halted because the patient is likely sleeping, but information from a sensor indicates that the patient is still clearly awake (using stringent criteria), then stimulation continues rather than being halted. Moreover, additional measures (e.g., heart and respiration rates, eye activity) are sensed and evaluated in order to determine if a patient is sleeping or awake. Only complete cessation of stimulation is described; halting the sensing and evaluation protocols is not mentioned.

U.S. application Publication No. 20040215286 to Stypulkowski ("the '286 application") controls therapy by means of a base stimulation program and one or more patient condition algorithms. The base stimulation program is modified according to the patient condition algorithms to generate multiple neurostimulation programs. The base program serves as a starting point for the generation of multiple neurostimulation programs tailored to patient activities. The patient condition algorithms may correspond to different patient conditions such as awake and sleeping or patient activities, such as sitting, and exercising. This strategy constrains the range of the possible parameter values (and permutations) used to provide stimulation, by using a base program as a starting point for subsequent modifications. Further, the patient condition algorithms only relate to adjusting characteristics of stimulation such as "pulse amplitude and pulse width". No mention is made of altering any sensing or evaluation routines in order to be responsive to different types of medical events, or in order to save energy, while the patient is in one state or another. The stimulation program is selected in one of two manners, either manually based entirely on input from the patient or automatically based on a sensed condition.

Two additional publications should also be noted; these provide methods by which treatments of implantable stimulation devices are adjusted in conjunction with patient input. In U.S. application Publication No. 20040199215 to Lee et al. ("the '215 application"), a clinician programmer may maintain a session log for the patient that includes a listing of programs delivered to the patient and rating information, provided by a clinician and the patient, for the listed programs. The subsequent selection of therapy programs is improved since highly rated programs can be selected with priority. In U.S. Pat. No. 6,986,347 to Hickle ("the '347 patent"), an apparatus and method are described for providing a patient relief from pain and anxiety associated with medical or surgical procedures. In this case a computer system is used to dispense medication. The patient may make a request for an increase or decrease of drug therapy, and the physician approves or denies the requested change.

It would be advantageous for systems and methods to address certain shortcomings in the known approaches, and to provide adaptive therapy programs based on calculated patient states and expressed preferences, computed from time information, sensed information, and patient input. The current invention offers a number of advantages that address the shortcomings of the prior art and provides other novel features as will be made clear.

SUMMARY

Systems and methods are described for adjusting treatment, during different periods, as the treatment needs of the patient vary. In one embodiment, the stimulation system has a clock which provides time information which is used while determining patient state. The system may automatically revert to a sleeping protocol at a time when the patient is usually sleeping and revert to a waking protocol near a time when a patient normally awakes. The system may also use sensed data to determine the state of a patient. Patient state is used to make a change in the treatment such as adjusting the sensing, stimulation, and evaluation protocols. Unlike known systems, a system according to the invention may automatically alert the patient to a proposed adjustment and wait a selected duration for approval from the patient for this adjustment prior to making the proposed adjustment. Patient alert rules are provided which allow the device to continue to operate according to the response of the patient or even when the patient does not respond. These rules can be implemented by a therapy control program which automatically alerts the patient to a proposed adjustment, obtains input from the patient with respect to the proposed operation, and operates the device, according to these rules, while waiting for this input. The system also can include a treatment program which selects which of two or more protocols to use based upon patient state information and can adjust particular parameters of a protocol according to this information. The invention provides a number of methods that utilize, and systems which implement, treatment which is adjusted based upon changes in patient state.

Four advantages treatment features are primarily realized by the methods and systems of the present invention. A first feature automatically alerts patients by providing notice before adjusting or providing therapy, and rules are provided for operating according to patient's response to the alert. A second feature adjusts the evaluation and sensing protocols based upon patient state. A third feature implements hierarchical treatment methods wherein operations that occur at higher stages are contingent upon operations at lower stages. A fourth feature dynamically changes priority rules, based upon specific times or events. In various embodiments, the invention can be implemented fully or partially within an implanted treatment device, a patient programmer, or a separate device which communicates with either of these (e.g., a computer that may, or may not, be connected to other computers over the internet; or, an implanted device that communicates with one or more implanted stimulation devices). A system according to the invention can be programmed to switch among protocols primarily automatically, or semi-automatically, or both (concurrently or alternatively, depending upon events). The invention can be combined with other known methods. As will be described in further detail below, these features can be used either separately or in combination to provide a multitude of advantages to the patient. A number of variations and advantages will be described for each feature.

Accordingly, an embodiment of the invention provides a system and method of providing therapy, wherein adjusting a treatment protocol includes determining that an adjustment in the treatment protocol should occur, alerting a patient to a proposed operation by providing an alert signal, and said adjustment in the treatment protocol occurring, or not occurring, only after a "response condition" is evaluated as true. A response condition may be evaluated as true due to an "accept" or "reject" patient response from the patient, an expiration of a time limit without a response (i.e., "no response"), a presence or absence of a defined sensed condition having priority, or any of numerous other possibilities. Illustrative patient response rules which guide the operation of the device while awaiting a response, until the response condition terminates, will be described in detail below.

In an embodiment of the current invention, a method of adjusting a treatment protocol includes determining that an adjustment should occur, alerting a patient to a proposed adjustment in the treatment protocol by providing an alert signal, and performing the proposed operation only if the patient approves the adjustment or a time limit is reached.

In an embodiment of the current invention, a method of adjusting treatment operations includes determines that an alert event has occurred, notifying a patient with an alert signal, adjusting operation according to the patient's input response. In addition to approving or rejecting the proposed operation, the patient may also delay the proposed adjustment, request a reminder alert, modify the suggested adjustment, or choose between 2 or more proposed adjustments. The alert signal can also include a request to answer 1 or more questions, the answers to which can be used to semi-automatically modify treatment.

According to an embodiment of the invention there are provided methods for automatically sending alerts to the patient in order to accomplish at least one of the following to resolve conflicts between time and sensor information (or to one piece of information out of several within each category); to resolve conflicts between two or more types of sensor information; to assign priority to time or sensor information; to select a priority rules; to alert the patient about a proposed adjustment; to request that a patient set an order of priority rules; and, to provide a response that assists with the evaluation of sensed data or other operation related to provision of therapy.

According to an embodiment of the invention, patient alert rules determine what type of alerts signals are sent to the patient according to different alert events, how long to wait for a reply from the patient, what to do while waiting, what to do in the case of multiple alert events occurring over a short period (e.g., according to the history of alert events, or in the case of overlapping alerts), and what to do in the case where the patient does not respond to an alert message having waited the predetermined amount of time. A device according to the invention may be operative to send an alert signal prior to providing at least one type of selected therapy, such as stimulation over a specified amount or duration, and the stimulation may be provided according to a change in patient state or in response to a detected medical event.

According to an embodiment of the invention, pre-emptive stimulation strategies may be used to automatically send alert signals related to anticipated future events, even when no medical events requiring treatment have been detected. It will be recognized that treatment may be adjusted in a system according to the invention based on an anticipated patient state rather than the patient's current state.

According to an embodiment of the invention, various combinations of automatic, manual, and semi-automatic types of methods may be used in a system according to the present invention to provide treatment, where a method type can be set to occur accordingly to user preference at different times, concurrently with a different method type, in response to various patient states and the detection of different events, and according to threshold criteria.

Moreover, as well as adjusting control laws, sensing and evaluation protocols may be adjusted based upon patient state information, to realize control laws, and alert messages may be sent automatically prior to such adjustments being implemented.

Accordingly, then, an embodiment of the invention provides adjustment of the sensing and evaluation protocols at different times and under different conditions. Under the adjusted protocols, different types of events can selectively lead to stimulation treatment, wherein one type of adjustment requires events to be of a larger magnitude (i.e., than is used during other states) during a patient state for which the treatment therapy is less needed by a patient. For example, a sleeping protocol may be enabled, in which stimulation only occurs in response to events which are detected using a second threshold which is different from (e.g., larger than) a first threshold that used when the patient is awake.

In an embodiment of the invention, sensed data are evaluated based upon an evaluation protocol that is adjusted continually, periodically, or occasionally based, at least partially, upon the patient state. Further, sensing and evaluation protocols can be altered based upon patient state values and the stimulation protocols are then adjusted contingent upon the selected sensing or evaluation protocols. In an embodiment of the invention, this pairing of sensing, evaluation, and stimulation protocols is defined using S-EVA-S set rules which can be defined in and implemented by the treatment program.

An embodiment of the invention provides varying methods of treatment, wherein conflicting data are resolved automatically, using dynamic priority rules or by providing notice to the patient and acting differently depending on the patient's response, if any.

An embodiment of the invention provides treatment using multi-level sensing and evaluation protocols, and hierarchical algorithms, in which a secondary protocol is enabled only if a first level condition is satisfied. More complex or comprehensive processing and evaluation of sensed data may be configured to occur only if less complex operations have met a level criterion, such as the detection of a certain clinical event. For example, sending data to an external programmer for further analysis or sensing from a second set of sensors can occur in higher level protocols using a multi-level algorithm. In an analogous manner, treatment parameters and treatment protocols may also be varied according to similar hierarchical analysis of conditions, detections, and patient inputs. Patient input can be used to meet a level criterion.

An embodiment of the invention provides treatment which adjusts by a clinically relevant and significant amount at least one therapy parameter, such as its duration, location, amplitude of stimulation, or dosage during a patient state for which the treatment therapy is needed more or less by a patient. Alternatively, different treatment protocols may be selected, at least one of which adjusts by a clinically relevant and significant amount some metric of therapy intensity. For example, a sleeping protocol may decrease stimulation during sleep, stimulate intermittently or irregularly rather than continuously, or otherwise modify the type, location, or dose of electrical or pharmaceutical stimulation. The adjustment can cause the amount of stimulation to change by a significant amount which is, for example, at least 30%.

An embodiment of the invention provides an implantable stimulation device that contains protocol sets of at least tow or more sensing, evaluation, and stimulation protocols that may be adjusted based upon patient state information.

An embodiment of the invention includes an implanted programmer-timer capable of estimating or calculating patient states relevant to the provision of therapy, wherein the implanted programmer-timer communicates with a generic implanted stimulation device either directly or via an external patient programmer to effect changes in treatment according to the patient state.

An embodiment of the invention provides a method wherein therapy is adjusted for a network of two or more implanted stimulator devices. For example, bilateral stimulation can be applied in an alternating manner using a diurnal cycle. Hence, the methods and systems of the current invention can be implemented as an independent device which can communicate with an implantable stimulator, or a network of stimulators, to deliver treatment according to the principles described herein in order to provide improved therapy to the patient.

The current invention offers a number of objects and advantages that address certain shortcomings noted in known approaches, and also provides other improvements as will be made clear in the following description of the inventive methods and systems and the associated figures and claims. The current invention implements the foregoing aspects and features, alone or in various advantageous combinations, in order to provide improved therapy to the patient. Especially when implemented within fully automatic, closed-loop devices, the addition of these features will provide increased therapeutic benefit a portion of the time.

BRIEF DESCRIPTION OF THE DRAWINGS

For the purpose of illustrating the invention and its advantages, there is provided a detailed description and accompanying drawings of embodiments which are presently preferred, it being understood that the invention is not intended to be limited to the precise arrangements and instruments shown, and wherein:

FIG. 5 is a schematic block representation of a method for selecting protocols in accordance with an embodiment of the present invention, wherein patient state information is used to select protocols for treatment;

FIG. 6A is a schematic block diagram of another method in accordance with an embodiment of the present invention, wherein alert signals are automatically provided to the patient and alert rules are used to semi-automatically guide treatment;

FIG. 6B is a schematic block diagram of another method in accordance with an embodiment of the present invention, wherein alert messages are automatically sent to the patient, and patient responses are used to semi-automatically guide treatment;

FIG. 7 is a schematic block diagram of a method in accordance with an embodiment of the present invention, wherein changes in a patient's state adjust treatment according to patient state rules;

FIG. 8 is a schematic block diagram, of another method in accordance with an embodiment of the present invention, wherein classification of a patient's state automatically adjusts treatment;

FIG. 10A shows a schematic representation of a general hierarchical method for applying two treatment protocols as indicated by level criteria;

FIG. 10B shows a schematic representation of a hierarchical method where at least one of a higher-level set of treatment protocols is selected using multiple level criteria;

DETAILED DESCRIPTION

The definitions of terms written in this specification shall be consistent with the context in which the terms appear and the ordinary broad meaning of such terms as would be understood by practitioners of ordinary skill in the arts relevant to the invention; withstanding that, exemplary definitions (which are illustrative but shall not be considered limiting) are included at the end of the specification.

Figure 1A:
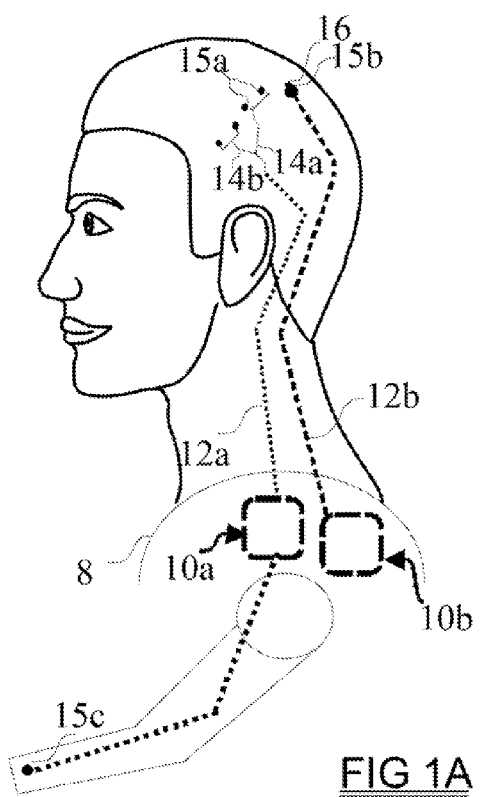
FIG. 1A shows an embodiment of the invention in which an electrical stimulator and a drug delivering stimulator are implanted to provide neurostimulation to a patient's brain.

FIG. 1A shows a patient 8 implanted with a neurostimulation system including a stimulator device 10a. The stimulator 10a may be implanted in the chest area, or it may be located within the skull, in the brain, or in any other location within the patient. Alternatively, the stimulator 10a may be partially external. At least one stimulation conduit 12a is provided which is positioned to stimulate a specific site in a patient's brain. In the figure, the stimulation conduit 12a comprises two leads 14a, 14b that are implanted into different areas of the brain. The two leads 14a, 14b can each have one or more electrical contacts 15. A selected stimulation protocol can specifically provide stimulation at one or more of the electrical contacts 15 of the leads 14a, 14b. When used to treat a central nervous system (CNS) disorder, the stimulation conduit 12a may be realized as any lead designed for stimulation of the spinal cord, cranial nerves, vagus nerve, or other tissue of the patient that is part of or can modulate the CNS. As is also shown in FIG. 1A, the stimulation conduit 12b can be realized as at least one catheter, which provides drug delivery to an output 16 at a desired tissue location from a drug pump stimulation system 10b. When the stimulator 10b is used to treat various disorders, the stimulator conduit 12b may be a catheter designed to deliver one or more drugs which are able to modulate tissues, organs, and biological processes related to the disorder, such as intrathecal drug delivery of morphine in the treatment of pain. The wall of the catheter can contain electrical communication means that have a proximal section which connects to the stimulation system 22 (FIG. 2) via routing circuitry in the control subsystem 20 and a distal end which terminates at a contact 15b. The contact 15b can provide both electrical stimulation and sensing. A separate contact 15c is located peripherally, and is used to sense electromyographic (EMG) activity in a limb. As is well known, when a drug infusion system 10b is used, this can include a pump and at least one reservoir for storing at least one drug to be delivered via at least one catheter having at least one lumen. Exemplary drug infusion systems capable of employing the present invention are disclosed in U.S. Pat. application Pub. Nos. 20060173406, 2004220552, 20040153029; 20040127942; 20040059315, 20040193255; 2005154370; and 2003199813; PCT Publication WO2005-007223; and U.S. Pat. Nos. 7,025,743; 6,902,544; 6,999,854; 6,269,340; and 5,975,085. The invention may be implemented within a system similar to the Paradigm™ drug pump for providing insulin in the treatment of diabetes. The invention can also be implemented within various types of emerging chip-based drug delivery systems, some of which may not utilize a catheter.

Figure 1B:
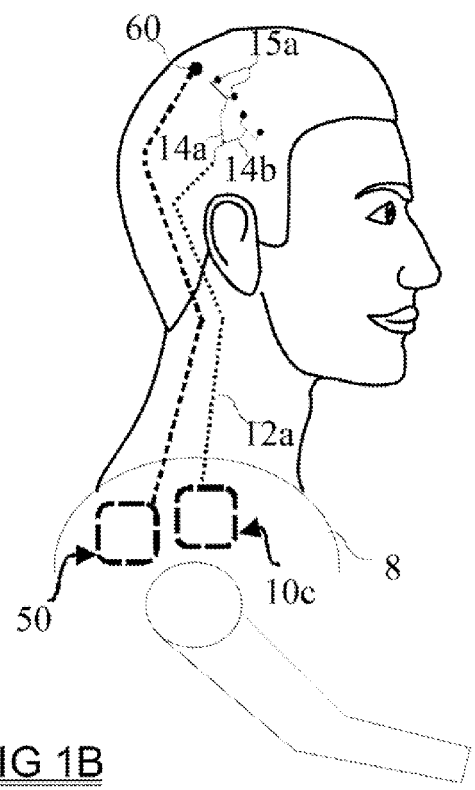
FIG. 1B shows an alternative embodiment of the system of FIG. 1A in which some sensors and stimulators are physically distinct and in which a timer-programmer is used.

Treatment can also include magnetic, optical, and other types of stimulation intended to modulate biological activity. Stimulation devices may be implanted in the body to modulate the activity of different tissues such as the heart, digestive system or other anatomical targets. Alternatively, stimulation devices can be implanted within the brain, or within the skull, and may stimulate the brain in order to modulate targets in the body, such as the heart, indirectly through the descending tracts of the nervous system. FIG. 1B shows a patient in which both a stimulator 10c and a timer-programmer 50 have been implanted. The timer-programmer 50 (which may be coupled to a sensor 60, such as an optical sensor) is an accessory which works in conjunction with generic stimulators in order to modify their operations. The stimulators 10 and timer-programmer 50 can be configured or adapted to provide treatment by adjusting protocols according to a patient's state, automatically providing alert signals, and to otherwise operate according to the features of the invention as described herein.

Figure 2A:
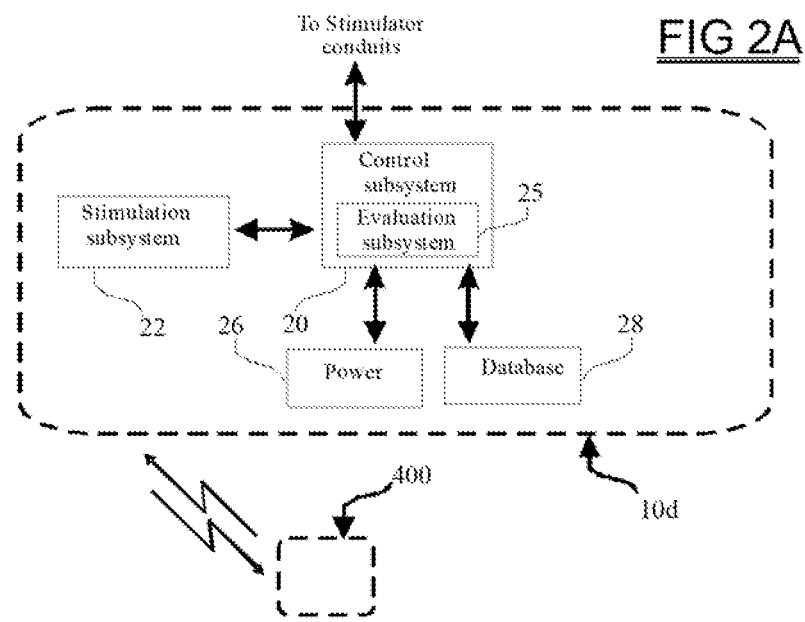
FIG. 2A is a schematic representation illustrating the components of a stimulator according to an embodiment of the present invention.

FIG. 2A is a schematic representation of an embodiment of a stimulator 10d (e.g., similar to the electrical stimulator 10a), which includes a control subsystem 20, a stimulation subsystem 22, an evaluation subsystem 25, a power source 26, such as a rechargeable battery, and a memory storage structure such as a database 28. The control subsystem 20 contains electronics which are commonly incorporated into implanted devices such as specialized circuits for carrying out the tasks involved in providing stimulation therapy (see, e.g, U.S. Pat. Nos. 6,066,163 and 6,810,285). The stimulation subsystem 22 can include hardware needed for the generation and transduction of different waveshapes used during stimulation according to the stimulation protocol. For example, a programmable signal generator (with amplifier circuitry) capable of generating charge-balanced biphasic pulse trains having programmable amplitude, frequency, and pulse width characteristics. The stimulation subsystem can also include a signal routing circuitry for routing the stimulation signals to one or more of the appropriate contacts 15 of the stimulation conduits.

Figure 2B:
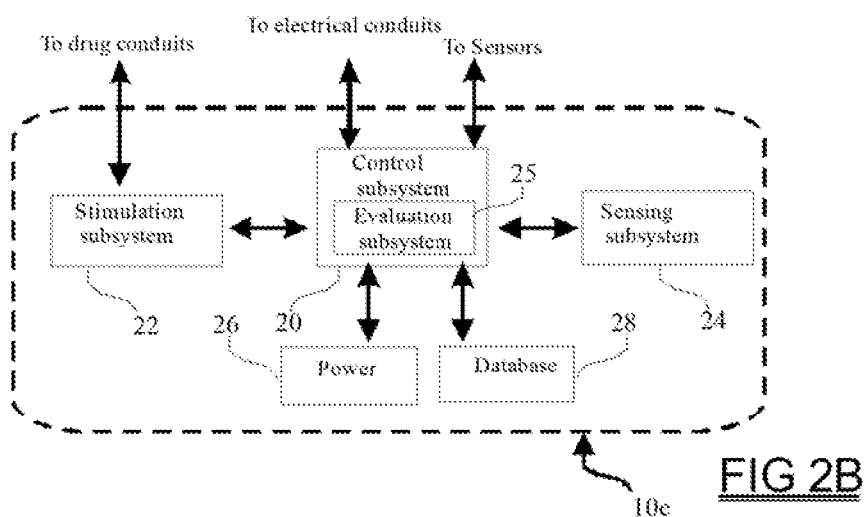
FIG. 2B is a schematic representation of the components of a stimulator according to an embodiment of the present invention, wherein the stimulator includes a sensing subsystem for sensing data from the patient.
Figure 4:
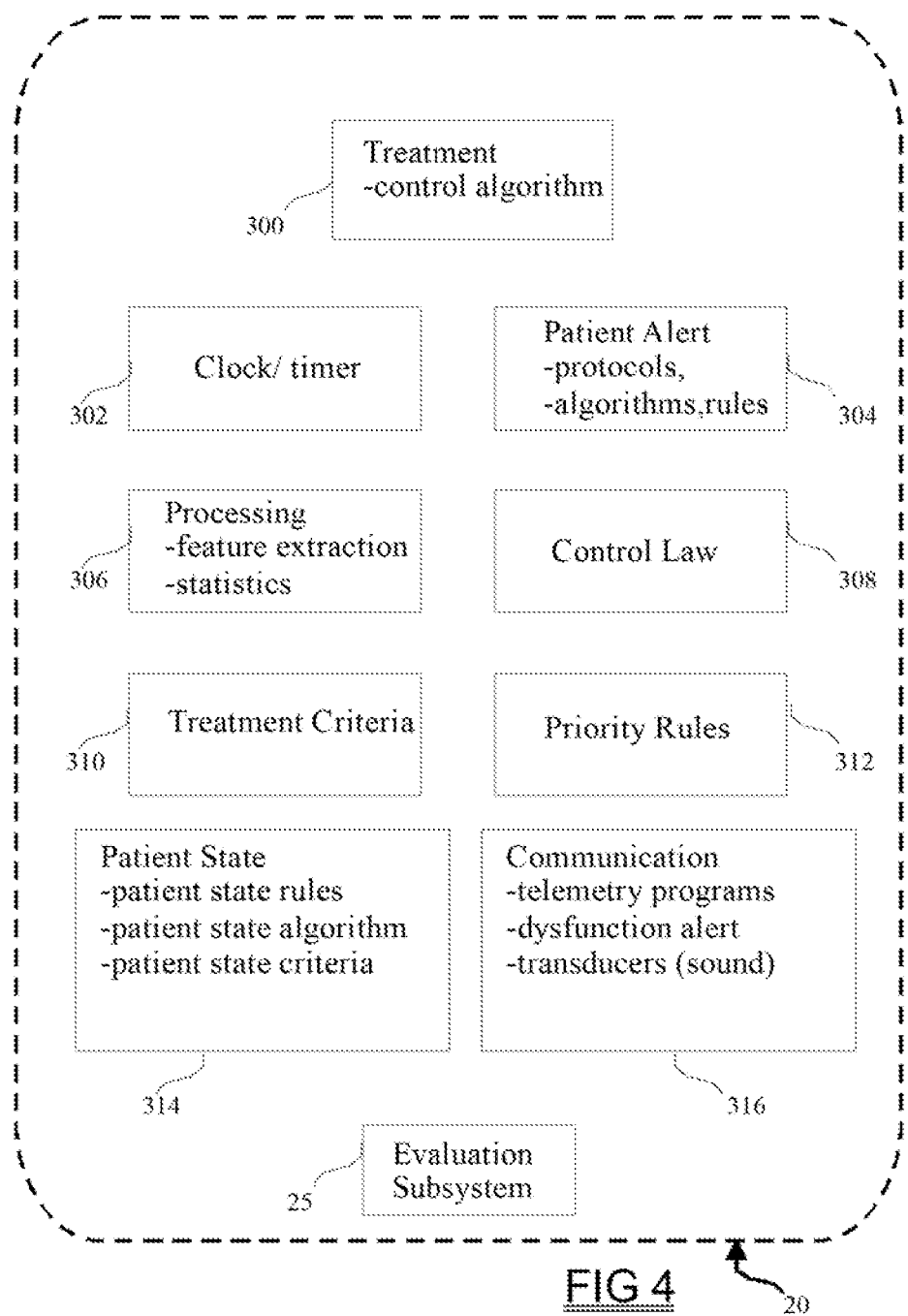
FIG. 4 is a schematic representation of the modules of a control subsystem according to an embodiment of the invention.

FIG. 2B is a schematic of the components of another embodiment of the stimulator 10e and includes a control subsystem 20, a stimulation subsystem 22, a sensing subsystem 24, an evaluation subsystem 25, a power source 26, and a database 28. The sensing subsystem 24 can provide any analog-to-digital conversion circuitry, memory, multiplexing circuits, relay, signal processing circuitry, or other circuitry which is not provided in the control subsystem and which is needed to obtain, process (e.g. filter), analyze, amplify, and store the sensed data obtained from at least one sensor. The sensing subsystem 24 senses data and performs processing and analysis according to the parameters of a sensing protocol. Analysis of the sensed data can include feature extraction of time, frequency, or time-frequency domain features of the data. The sensing subsystem 24 can calculate quantitative results which it provides as processed data the control subsystem 24, although the control subsystem can process the raw data itself 306 (FIG. 4). The evaluation subsystem 25 is a module of the control subsystem 20 that can evaluate processed data using an evaluation algorithm that operates according to a protocol, and can perform additional processing and evaluation of the data that was not accomplished in prior steps by the sensing subsystem 24.

In an embodiment of the invention, the sensing and evaluation protocols are adjusted by a control program. For example, each protocol may be selected from a set of two or more protocols. Such selection can be determined by patient state which is determined when the control program that is implemented by the control subsystem 20 operates to compare pre-set times stored in the database 28 to the time information provided by a clock 302 (FIG. 4) and determines a match (e.g., steps 70 and 72 of FIG. 5). In other embodiments the sensing and evaluation protocols are selected based upon a patient state which is computed from sensed data (e.g., steps 116 of FIG. 8). As will be described below, time and sensed data information may both be used to calculate a patient state value that is then used to adjust or select a treatment protocol.

It should be noted that the conduits (e.g. 12*a*, 12*b*, shown in FIG. 1A) can provide both therapy delivery and sensing. For example, each contact 15, can be used both as a sensor, wherein the stimulator conduit functionally communicates with the sensing subsystem 24, and as a stimulator, wherein communication occurs with the stimulation subsystem 28. The physical connection between the contact 15 and the sensing 24 and stimulating 22 subsystems, can be controlled by a micro-relay or switch which can be located in the control subsystem 20 circuitry, such as a make-before-break double-throw relay. Alternately, as shown in FIG. 1B, sensors 60 and stimulators 15 may be physically distinct, for example, as may be the case when the sensors 60 measure optical, chemical, pressure, temperature, movement, or other physical aspect of the region from which the sensed data are obtained. As is illustrated, the electrical stimulation/sensing can be medicated directly by the control subsystem 20, or can be accomplished by means of the stimulation 22 and sensing 24 subsystems which are under control of the control subsystem 20, as is the case for drug delivery. If the stimulation entails the delivery of drugs, then the drug can be directly dispensed through the drug conduits 12*b* by the stimulation subsystem 22 of the drug delivery system 10*b*.

External Timer-Programmer.

Figure 3A:
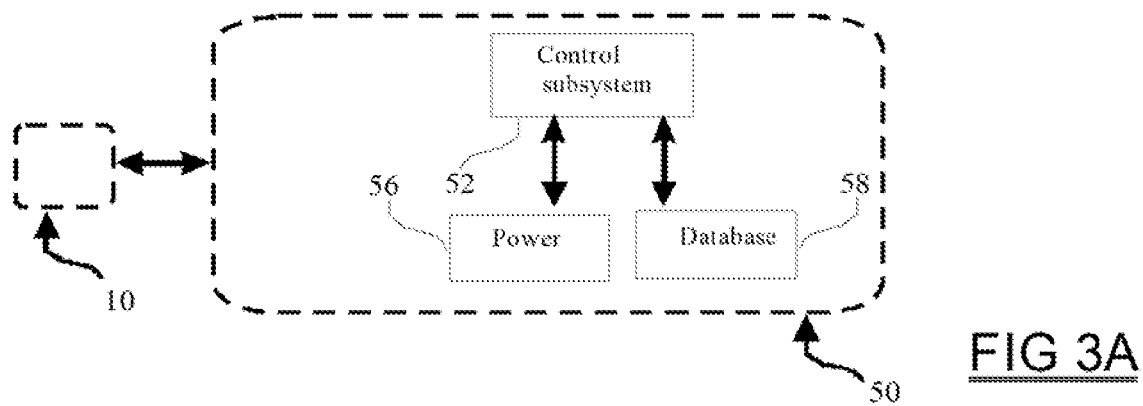
FIG. 3A is a schematic representation of an implanted programmer-timer according to an embodiment of the invention, wherein the programmer-timer adjusts the operation of a generic stimulator.

As was shown in FIG. 2B, the invention can be realized in a distributed embodiment. FIG. 3A shows an embodiment of the invention wherein a timer-programmer 50 is used to provide features of the invention. The timer-programmer can be (but need not be) implanted fully in the patient and can communicate with a generic stimulator 10 or its patient programmer. The timer-programmer 50 can communicate, via the communication module of its control subsystem 2 with the communication module 316 of the control subsystem 20 of the stimulator 10 in order to guide treatment according to the principles of the invention. The programmer 50 can contain a control subsystem 52 that is similar to the control subsystem 20 of the device 10 and a database 58 containing, for example, times at which different protocols can be selected, the parameters for each protocol, and an "alert event set". The timer-programmer 50 can also include a power supply 56. The timer-programmer 50 does not need to have a stimulation module, as the stimulation module of at least one device 10 serves this purpose.

The timer-programmer 50 can be implanted as is shown in FIG. 1B or, alternatively, can be realized in external embodiments. For example, the timer-programmer 50 may be incorporated into a watch-like mechanism that serves as an external patient programmer 500 and is worn on a patient's wrist. The timer-programmer 50 can be realized in the form of a software module of an external patient programmer 400 that works with the stimulator 10. In an embodiment of the invention, the external patient programmer 400 and the communication module 316 of the stimulator 10 each include a transceiver operable in the MISC (Medical Implant Communications Service) band around 400 MHz, enabling communication between the devices over a range of several meters. An implanted timer-programmer 50 can server to turn the stimulation device 10 "on" or "off", can automatically send alerts, and can provide other features of the invention. The timer-programmer 50 thereby allows generic stimulators, which are already FDA approved, to provide treatment according to timing or other information, even if this capability is not normally available in the generic device 10. The timer-programmer 50 contains a control subsystem 52 which can approximately contain the elements previously described for the control subsystem 20 including a real-time clock and any components not included in the device 10 which are needed to implement the features of the invention. An externally situated timer-programmer 50 allows for somewhat more complex control programs and algorithms, and as such a device would not necessarily be constrained by the same limitations of size and power consumption as an implanted device.

Figure 3B:
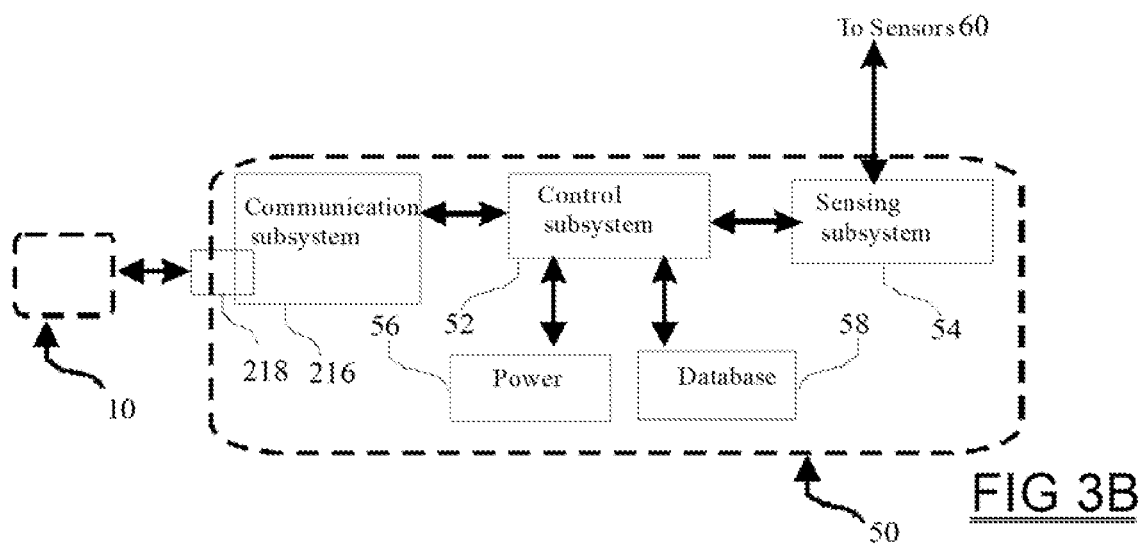
FIG. 3B is a schematic representation of the components of a programmer-timer according to an embodiment of the present invention, wherein the programmer-timer utilizes information obtained from a sensing subsystem of a generic stimulator.

FIG. 3B shows an alternative embodiment in which the timer-programmer 50 includes a sensing subsystem 54 that communicates with at least one sensor 60 adapted to collect information from the patient, thereby allowing the timer-programmer 50 to adjust treatment, for example, based upon patient state values derived from sensed data. Alternatively, if the implanted device has sensors, then the timer-programmer 50 can use sensed data which is obtained by the device 10 and transmitted to the timer-programmer 50. If the timer-programmer 50 is expected to perform a relatively large amount of communication with the device 50, it may include a communication subsystem 216 as a separate subsystem and, rather than using telemetry, the timer-programmer 50 can have a physical communication port 218. This port 218 allows a physical connection to be made between the timer-programmer 50 and at least one implanted device 10 which is also configured with a communication port so that a physical link can connect the two devices. A physical connection may require less power than using telemetry. A single-wire connection, using the patient's body as a reference, may be used for the connection to reduce complexity and the likelihood of mechanical failure, although it is likely that a multi-stranded cable would be implemented for providing both efficient communication and the sharing of power.

The timer-programmer 50 can be programmed to communicated with most commercially available stimulators that are already designed to communicated with the external patient programmers provided by a manufacturer. To accomplish this, the communication subsystem 216 (as may also be realized by 316) can include routines for identifying an implanted stimulator and external patient programmer 400, establishing communication, making error and parity checks, dysfunction alert routines to alert the patient in the case of breakage, and alert routines for automatically notifying or querying the patient about treatment operations that have been defined as alert events. When the programmer 50 has a clock, the control subsystem 20 of the stimulator 10 may, or may not have a clock. FIG. 1B shows a patient in which both a stimulator 10 and a timer-programmer 50 have been implanted, and wherein the timer-programmer 50 has a sensor 60 which is used to adjust or select the stimulation, sensing, or evaluation protocols based upon either timing or sensed information according to the features of the invention. When a physical connection is present, then the stimulator 10 may not require its own power source, and the timer-programmer 50 can supply power to the stimulator 10. Conversely, the timer-programmer can obtain power from the stimulator 10. In an embodiment of the invention, the control subsystem 52 of the timer-programmer 50 may function to approximately replace a majority of the components and capabilities of the control subsystem 20 of the stimulator 10.

Control Subsystem.

FIG. 4 shows an overall block diagram of an exemplary control subsystem 20 that allows devices to implement features of the current invention. The control subsystem implements the treatment program according to the control algorithm of the treatment module 300. The treatment module 300 contains the treatment program, which may be part of or interact with the control algorithm, and implements the treatment program by communicating with, coordinating, and controlling the modules of the control subsystem 20 and their operations. The control subsystem 20 serves to realize the treatment program by controlling the stimulation subsystem 22, sensing subsystem 24, and evaluation subsystem 25, according to stimulation, sensing, and evaluation algorithms and associated protocols. The control subsystem 52 of the timer-programmer 50 or the external patient programmer 400 can include all or some of these components, although these would be adapted to control a generic stimulator device 10c rather than being located within the stimulator itself. Accordingly, the control subsystem 20 may be implemented either as a single component within the implanted device 10 or exists as distinct modules distributed throughout a system.

At various times prior to, during, or after implantation, the control subsystem 20 can be programmed to adjust therapy in relation to predetermined times. The times may be, for example, absolute number of counts of the clock, relative durations (e.g., times since the last stimulation protocol was selected, time since last stimulation occurred, and cumulative amount of time that stimulation has occurred over a recent period using current protocol), or times of day. Using an external patient programmer 400 (FIG. 2A), the patient may adjust the time values stored in the database 28 which are used by the treatment program implemented by the control subsystem 20 in order to select or adjust treatment protocols according to specific times. For example, one protocol can be selected to occur just prior to when the patient usually wakes up, and another protocol can be selected to occur after a specific time in the evening after the patient has normally fallen asleep. Protocols can also be automatically adjusted based upon times and periods when a patient normally eats, works, exercises, or experiences higher levels of anxiety or depression. This adjustment can be programmed to occur prior to anticipated events, or during such events, and may extend until after the event ends. During the course of treatment, the time values can be adjusted using the external patient programmer 400 to reflect changes in the patient's schedule, as may occur, for example, due to daylight saving time, travel to different time zones, an acute event, etc. A clock 302 of the control subsystem 20, which may be a real-time clock or simply an interval timer, provides times information which may be used in calculating a patient state value or otherwise adjusting therapy. For example, the clock 302 permits the control subsystem 20 to select a protocol from two or more protocols stored in memory, or to adjust at least one parameter of a protocol (such as the operative stimulation protocol) based upon time information.

The patient state value may be used by the control subsystem 20 to determine that a protocol will be adjusted. The control subsystem 20 can utilize an algorithm which compares the current time of the clock to time criteria (e.g., time=11 p.m.) in order to determine the patient state value or determine that some operation is scheduled to occur. This time algorithm is part of the treatment program which uses a treatment protocol that has parameter values, some of which are selected times relevant to therapy. Because the clock 302 of the implanted device can drift over time, the clock 302 used by the control subsystem 20 can be adjusted or calibrated using at timing signal that is provided by the external patient programmer 400.

The control subsystem 20 also contains a patient alert module 304 configured to automatically provide notice to the patient of "alert events", using signals and obtain patient input in response to these alert signals. The patient alert module 304 implements a patient alert algorithm that uses patient alert rules to provide the alert signal and also to obtain and process patient responses. The algorithm can assess if alert events have occurred, and can be informed that these have occurred from other modules of the control subsystem 20. Alert events include any operation (e.g., medically relevant events) which is defined as requiring that an alert signal be sent, as may be defined in the "alert event set", which is programmed into a data base 28, or into the patient alert algorithm itself. For example, the patient alert module 304 can automatically send alert signals to notify the patient about the pending implementation of any treatment operations (which are defined as alert events) and also to await a response from the patient. In addition to the provision of therapy, when any adjustments in operation are scheduled to occur, and these are alert events, then the patient alert module can automatically send an alert signal to a patient announcing the proposed adjustments. The characteristics of the alert signal which is provided can be defined according to the patient alert algorithm using patient alert rules of the patient alert module 304, can be defined separately in an "alert signal set", or can be part of the alert event set and be stored as information that is accessed when their respective alert events occur.

The patient alert module 304 may cause the communication module 316 to send an alert signal to the external patient programmer 400 which can alert the patient using its own methods and transducers. An alert signal, such as that implemented in step 86 of FIG. 6A, can cause the external patient programmer to emit a visual, auditory or vibrotactile alert signal as well as text-based message. The alert signal may require various responses from the patient, such as an "accept" response, a "multiple choice" response invoked by a request that the patient choose from multiple options, or "score" response, invoked by a request to assign a weight or score to a particular value (e.g. a response may include asking a patient to rate his or her pain level on a defined scale). Additionally, the communication module 316, itself contains various transducers to provide alert signals in the form of auditory tones, vibrotactile signals, somatosensory electrical stimulation patterns, and other modes and combinations, according to the alert signal that was selected by the patient alert module 304. For example, an auditory signal which repeats 3 long beeps 2 times might signify that the system is going into a "sleep" mode. The alert signal can occur simultaneously with a suggested operation, at least a minute or some other defined period prior to the time the proposed operation is scheduled to occur, or can be set to occur according to patient preference with respect to the proposed operation (i.e., the patient alert rules are configurable by the patient).

Patient alert rules include what to do if a "cancel alert" event occurs. A cancel alert rule is a type of patient alert rule that can defined both a cancel alert event as well as operations that are invoked. A cancel alert event may cause the prior alert signal to be turned off, or replaced, even if the patient has not provided a response. For example, a cancel alert rule may state that if the event which served as the prior alert event is no longer detected for a specified amount of time, then a cancel alert event has occurred and the prior alert signal is then cancelled. Alternatively, the cancel alert rule can dictate that the previous alert signal is replaced with a different alert signal if an alert event which has a higher priority occurs (e.g., if cardiac activity transitions from bad to worse, causing a detection of a first and then a second alert event, the detection of this latter alert event can have priority as defined in the priority rules module 312). A cancel alert event can thus result in either canceling or providing the operation suggested by the prior alert event. A cancel alert event can be a presence or absence of a defined sensed condition having priority over the alert event which invoked the previous alert signal.

The patient alert module 304 operates according to patient alert algorithm and its protocol which includes patient alert rules. The patient alert rules can be defined within the alert event set or be otherwise stored or accessed by the patient alert module 304. In one embodiment, the patient alert rules consist of two types of rules, the "send alert" rules and the "patient response" rules. The send alert rules determine, for example: what information is contained in the alert signal; what type of alert signal is sent as well as its modality; how the alert signal is adjusted over time if a patient doesn't respond (e.g., increasing the volume over time); what alert signal occurs if another alert event occurs while waiting for a patient response to a prior alert signal ("overlapping rule"); whether to provide a "missed" alert signal which notifies a user that an alert event occurred without the user providing a response; what to do if the patient state value changes or the alert event stops being detected (i.e. is "extinguished") while waiting for the patient to provide input ("transition rule"), and what to do in other situation, with respect to the adjusting the alert signal.

The patient response rules can include, for example, what to do: if a patient does not respond; while waiting for a patient to respond; if a patient accepts or rejects a proposed operation; for each response of a "multiple response" question; when a patient response is one of various possible values; if a patient delays an operation proposed by the alert signal; and what to do in other situations, with respect to the adjusting the operations carried out by the device. The patient response rules also determine how long to wait for a patient's response prior to implanting a particular operation. Patient response rules allow treatment algorithms to operation (e.g., provide therapy) even when a patient doesn't respond, such as may occur when the patient is in the shower, in a loud restaurant, or if the programmer is out of range. According, "no response" must be included a possible type of patient response. In the case of insulin delivery, if the patient doesn't provide an "accept" response to an alert signal which requests user approval for a dose which is above (or below) a specified level, the system must know what to do and can not simply halt its operation (e.g., the evaluation of incoming data and provision drug delivery) while waiting for a user response. In the case of a diabetic or cardiac disorder, abstaining from a proposed therapy indefinitely, while waiting for a user response, can cause a serious medical condition to arise. One type of patient response rule may state that a "no response" causes the intensity level of an alert signal to be increased over time according to a function which may vary with an alert signal type. Another patient response rule may state the "no response" causes the device to wait for a specified amount of time and then accept, reject, or modify, the proposed operation. Another "no response" patient response rule may wait for a patient response unless a type of additional alert event is detected within a specified amount of time (i.e., a "cumulative" rule). The cumulative patient alert rule may also dictate that the action suggested in the prior alert signal occurs, even without the user response. The user or physician can define the various patient alert rules and combinations of rules which will be utilized during treatment.

The patient alert rules can be designed to accommodate a large number of patient input responses. Some types of patient response are: "accept", in which the proposed operation occurs; "accept duration", in which the proposed operation and subsequent operations of the same type are accepted for a specified duration; "adjust", in which the user modifies the proposed operation; "delay", in which the user accepts the operation but delays its onset by a specified amount; "remind" in which the alert signal is repeated at a later time; "reject" in which the operation is rejected, "reject duration" in which the operation contained in the alert signal is rejected and all similar alert events are automatically rejected for a specified duration; and "more info" in which the user requests more information be provided before providing a patient response. The duration of a response condition can be increased if a patient provides a "delay" or "remind" input.

The patient alert module can store a limited history of past alerts in the database 28. The treatment program can cause the patient alert module to adjust alert signals, or cause an operation to occur without patient input based upon alert history, and according to patient alert rules. For example, if a selected number of alerts are sent within a selected amount of time (i.e., a "cumulative" rule), if the alert events become larger or more numerous over time ("trend" rule), or if a subsequent alert is issued while waiting for a prior alert (i.e., a "overlapping" rules, which can be implemented as a type of a cancel alert rule) then an operation, such as delivery of a proposed treatment, which may normally be an alert event may occur without patient input, or according to a response rule which waits only a slight period for patient response. In one embodiment, response conditions can be labeled as either positive or negative. A positive response condition may be evaluated as true due to a positive explicit response from the patient ("patient input=accept"), an expiration of a rejection time limit, a presence or absence of a defined sensed condition having priority, or any of numerous other possibilities. A negative response condition may be evaluated as true due to a patient's explicit request to reject a change, an expiration of an approval time limit, a presence or absence of a sensed condition having priority, or any of numerous other possibilities.

Various other forms of notification, according to varying degrees of urgency, are possible in a system according to the invention. For example, if the patient is likely to be disturbed during sleep by an audio signal, and such a high level of intrusion is unnecessary, the system may send a text alert signal to the programmer 400, allowing the patient to check for alerts when the patient awakens. In such a case, a flashing light may also be provided on the programmer 400, similar to voicemail indicators found on telephones.

The control subsystem also contains a processing module 306, while can be configured to extract features from the sensed data, as well as calculate statistical properties of these features such as mean, standard deviation and z-scores. The processing module 306 can also provide the database 28 with the calculated values in order to provide self-norm reference data which may be used for such purposes as calculation of the current patient state and determining if a patient state has changed, or storing the number of detected events (e.g., alert events) which have occurred over a recent period. The processing module 306 can also include filtering, classification, template matching, and other signal analysis modules. The processing module can process sensed data to provide processed data which can be used by the control law module 308 to generate output stimulation signals according to the control law selected in the stimulation protocol that is implemented by the control subsystem 20. The algorithms of the processing module can be utilized by the evaluation module 25 in the evaluation of sensed and processed data.

The control subsystem 20 also contains a treatment criteria module 310, which assists the evaluation subsystem 25 in comparing, for example, processed data or time information to treatment criteria. The treatment criteria module 306 loads treatment criteria values from the database 28 according to the selected evaluation protocol. The treatment criteria module 306 can detect medically relevant events which result in responsive stimulation. The treatment criteria module can include treatment benefit criteria which assist in calculating measures that are reflective of, for example, whether treatment is decreasing or otherwise altering the number or severity of detected medical events, compared to (mean values of) a reference treatment period.

The control subsystem 20 also contains a priority rules module 312, which can implement priority rules which may be set according to a patient's preference. A priority rule can be adjusted by automatically sending an alert signal requesting the patient to assign priority to one of two operations. Further, the priority rules module 312 can set priority rules dynamically according to patient state or for different operations. For example, for a "stimulation off" operation time information can have priority over sensed data, while for a "stimulation on" operation the opposite can be true.

The control subsystem 20 also contains a patient state module 314, which determines the patient state using data from the device (such as time data, patient response data, and sensor data) processed through the patient state algorithm and according to the patient state rules which may also incorporate the priority rules of the priority rules module 312. The patient state rules govern how to define and classify patient state and can also include rules about what operations may occur according to different states.

The control subsystem 20 also contains a communication module 316, which contains telemetry algorithm and hardware for communicating between different components of the therapy system such as the patient programmer 400. The module 316 also can provide dysfunction alerts in case the system encounters an internal error, is low on reserve power, or when it can contact the patient programmer 400. For example, the device may begin to emit an auditory signal which is audible by the patient when an alert signal has been triggered but the device 10 finds that it can not successfully communicate by telemetry with the programmer 400. The communication module 316 can then implement the instructions of the patient alert module 304 in order to send and receive information from the patient.

Figure 11A:
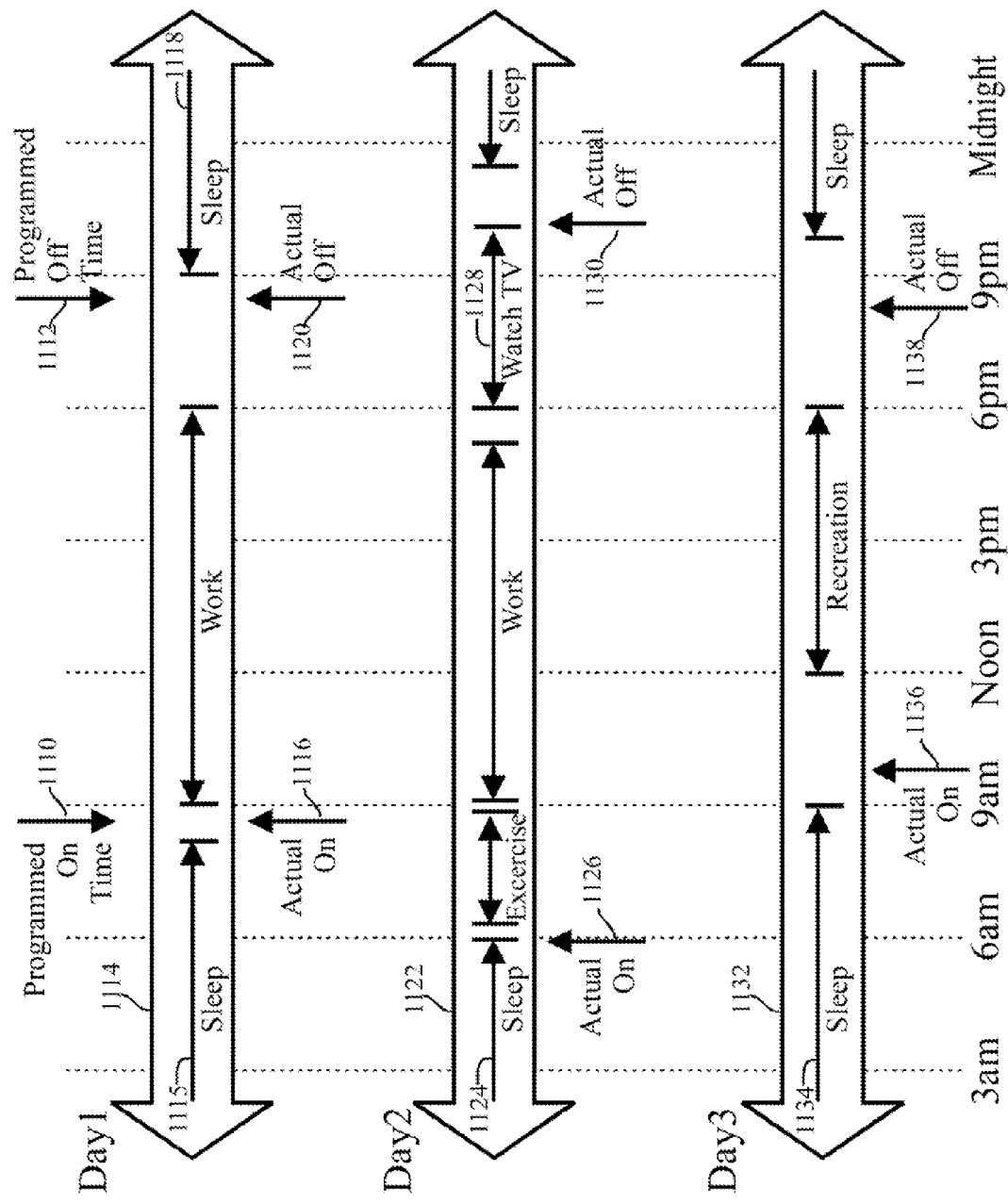
FIG. 11A is an exemplary timeline illustrating patient-directed selective therapy activation according to an embodiment of the invention.

The control subsystem is operated according to a treatment program 300 that implements a treatment algorithm. The treatment program 300 controls the operations of the components of the system to provide therapy. The treatment program coordinates the various modules of the system to work together so as to provide treatment. For example, the treatment program can rely upon the priority rules module 312 to cause the patient alert module 304 to automatically issue an alert signals, for only one of two approximately simultaneous alert events, according to patient alert rules, and may detect this event based upon an evaluation algorithm of the evaluation subsystem 25 that is selected by the patient state module's 314 algorithm operating in accordance with patient state rules. An example of how the treatment program combines features of the invention to provide improved therapy is shown in FIG. 11a.

The different protocols and their parameter values as well as other reference information utilized by the device 10 are stored and retrieved from the control subsystem's memory which can be implemented, at least partially, in the form of a database 28. The database 28 permits the control subsystem 20 to obtain information such as stimulation parameters for various stimulation protocols, self-norm data, and other information relevant to providing therapy. Such parameters and data may be pre-defined across a patient population, tailored by a physician or expert system for a particular patient's needs, or constantly refined by a system according to the invention; combinations are also possible depending on clinical need.

The control subsystem can also include various components such as programmable memory, a microprocessor, additional timers/clocks, multiplexors, switches/relays and other components which are found in the control subsystems of most implantable neural or cardiac stimulators as is known well to those skilled in the art. Although shown as separate components for purposes of illustration, the components of this and other figures provided within this specification can generally be realized on a single circuit board, and even a microchip which contains specialized circuitry for amplification, digital-to-analog conversion, digital and analog signal processing, memory, timing, clock, and communication circuitry which are powered by a power source. When the stimulator provides drug therapy, the electronics can supply control of, and power to, a pump for dispensing one or more drugs stored in a reservoir assembly according to the stimulation protocol. Having described the components of the systems the associated methods will be described which allow the implementation of the features of the invention during its operation.

Priority Rules

The control subsystem 20 may automatically select a protocol according to patient state in a closed-loop manner. For example, the sleeping protocol may be selected if evaluation of time data indicates that the patient is sleeping. Sensed data may also be used as an alternative to, or in conjunction with, the time information provided by the clock of the control subsystem 20. Accordingly, stimulation system can use either time or sensed data to determine patient state and provide closed-loop adjustment of stimulation treatment. When time information and sensed data information are in conflict as to what the current patient state value, priority rules can be used to resolve this conflict.

In the '784 application, referenced above, when time information is available, the stimulator 10 generally operates according to the sleep protocol at night and the awake protocol during the day, as indicated when the clock time information matches predefined times which define awake and sleep periods. Similarly, in the current invention when sensed data are also available, unless there is a clear indication that the patient is in a state other than that indicated by the time information, the patient state rules of the patient state module 314 can indicate that the time information has priority over sensed data in the determination of patient state by the patient state module 314.

While a default protocol of the patient state module sets a patient state rule that is a priority rule in which time has priority over sensed data, the patient state algorithm of the patient state module 314 can select a different priority rule if a patient state criteria for the sensed data is met which is stringent enough that the patient is almost certainly in that state. FIG. 5, shows an embodiment which is compatible with this method. First the clock is checked 70 and patient state is derived as is indicated by the time information 72 stored the database 28. Next, data are sensed 74 and the evaluation of sensed data indicates a present state 76 based upon sensed data. Next the patient state based upon time information is compared to the patient state as derived by sensed data 78. If the patient state based upon time information is compatible with the protocol selected based upon sensed data information 80a then the patient state is used to select or adjust the protocol which is used to provide treatment 84. Alternatively, if the patient state which is indicated by time information is incompatible with the patient state indicated by sensed data information 80b then the protocol which is used to provide treatment 84 is selected based upon patient state rules implemented by the patient state algorithm 82.

A patient state such as "asleep" can be determined based upon measures of sensed data related to eye movement (e.g., to detect REM sleep), blink rate, and position (e.g. to determine if the eyelids are open or closed), and respiration or cardiac or motion activity. There are also electrographic markers of sleep observable in the brain. For example, a determination of patient state can occur wherein if the patient's eyes are shut for longer than a specified period, as can be defined in a patient state criterion, then sensed data can have a priority and the sleeping protocol can be selected. The system may utilize an evaluation protocol that evaluates patient state using compound patient state criteria in two or more operations. For example, both an "eye shut" criterion, and an EEF criterion where a relative power shift to the lower frequency range is over a specified amount, are met (or are failed depending upon the logic of the comparison operation) in order to set the priority rule to give priority to sensed data in order to set the patient state value to "sleeping" and invoke the sleep protocol.

The patient state algorithm which is implemented by the control subsystem of the current invention can dictate patient state and is determined by time information rather than sensed data information unless the state information meets patient state criteria that most certainly indicates the patient is in a particular state (e.g. awake or asleep). Some of the references cited above describe a feature where a threshold parameter used to determine patient state from sensed data may be adjusted by the physician or the patient to provide increased benefit. Further, the patient has the option of manually turning the stimulation system "on" or "off".

The current invention improves upon known methods by providing a treatment program that automatically and dynamically selects different priority rules for different operation and for different points of the day, such as can be implemented as patient state rules by the patient state algorithm. For example, although a patient may be asleep when napping during the day and when sleeping at night, the patient may only want the sleeping protocol to occur during the night, even if sensed data certainly indicate that sleeping is occurring. Except on the basis of time, it is almost impossible to design the threshold criteria used by the patient state algorithm to distinguish between regular sleeping and napping. Further, the two activities may be identical with respect to many measures. By temporally adjusting priority rules during specific periods of the day the patient does not have to repeatedly adjust the thresholds used to detect different patient states during the course of treatment. This is also an advantage over known approaches because it decreases the computational requirements of the implanted device which might be needed to distinguish similar states of the patient and improves therapeutic benefit to the patient. Additionally, during times when time information has been defined as having priority over sensor information, the sensor information can be turned off, which can save power usage. Similar to priority rules, patient state or treatment criteria can be adjusted at different times.

The methods of the invention also include automatically sending an alert signal to the patient when time data and sensed data information contradict each other, wherein the patient's response to the alert signal determines which priority rules is selected. The priority rules can also be applied to resolve conflicts between chemical and electrical data. The selection of a priority rule can be contingent upon a threshold criterion related to patient state wherein only if the threshold is exceeded does the priority rule get implemented. For example, normally sensed data information related to electrical activity is preferred to sensed data information related to chemical levels, unless these levels are above or below a level defined in the criteria invoked during a particular patient state. In addition to patient activity defining patient state, electrical or chemical activity serve this purpose. For example, a patient state can be classified as a "low 5-Ht" patient state, when serotonin levels sensed at one or more sensors drop below a specified criterion.

Priority rules can be used to resolve conflicts encountered in providing or adjusting treatment, especially with respect to adjusting the stimulation which is provided. The sensed data from two or more sensors can e evaluated using logical operators in a conditional manner. For example, if data sensed at a first sensor and a second sensor are both above specified thresholds, then stimulate in a particular manner. This can be considered an example of using a "complex treatment criterion" according to the invention. While in the '328 patent multiple types of sensed data including electrical and chemical activity are used to responsively provide stimulation, no mention is made of want to do when different types of data indicate contradictory information, such as increased and decreased treatment benefit. This can be addressed using priority rules. Similar to determination of patient state, the evaluation protocol can be governed by priority rules of the priority rules module 312 when determining if responsive stimulation or adjustment of the treatment is provided. The use of dynamically adjusting priority rules should enable therapy to incorporate, and adapt treatment on the basis of conflicting information. In an embodiment of the invention, a device can use its patient alert module to automatically request that patients select a priority rule or make other decision which resolves conflicting information. It will be noted that various criteria may be evaluated within priority rules according to the invention, including but not limited to treatment criteria, time criteria, and patient state criteria.

Semi-Automatic Treatment with Automatic Patient Alerts

Modern implantable stimulation devices are increasingly incorporating treatment programs that provide more comprehensive types of automation in controlling stimulation. Both the providing and adjusting treatment may occur in a fully automatic fashion. For example, responsive stimulation is stimulation which is triggered in response to sensed data when analysis of the data results in detection of one or more abnormal medical events. Adjustment of the stimulation that is provided can be based upon characteristics of a detected event such as the magnitude of observed activity in a device operative to respond to epileptic seizures, or can be based upon some related state of the patient. Although treatment algorithms may utilize time information, or evaluate sensed data, to accurately determine the state of the patient and then automatically change the treatment protocol, this may not universally work well for all patients. Further, as mentioned, conflicting information can pose a problem: sensed data may sometimes indicate a particular state (a person is sleeping) while time data indicates that a different state is occurring (a person is awake). It is difficult for an implanted device to accurately and automatically resolve conflicting information, and adapt to variations in the patient's daily routine, or otherwise anticipate the therapy preferences of the patient. Rather than creating increasingly complex routines for automatic, closed-loop control, semi-automatic methods may provide improved therapy by allowing patients to guide therapy by responding to automatically generated alert messages.

A central factor in providing therapeutic stimulation is the variability of the patient's daily routine. Currently, there is no known semi-automated manner for easily enabling a patient to modify treatment, in instances when the patient intends to deviate from an expected schedule, for which the pre-designed program was configured. For instance, a patient may choose to remain awake for several hours past the normal time when he/she falls asleep but may forget to change the setting for the implanted device. If a neurostimulator automatically powers down at 9 p.m., while the patient will not go to bed until 11 p.m., the clinical benefit of the implanted device is decreased. A second issue is that more complex algorithms require more power and resources and are complex to adjust for individual patients. Further, patients may have different preferences at different times and it is impossible for the algorithm to anticipate these preferences.

While time and sensed data information can sometimes be resolved by an algorithm using priority rules, a device may have trouble automatically disambiguating two patient states which are physiologically similar, such as being in REM sleep or being awake, being nervous and being excited. Although these are distinct states, these are also physiologically similar in certain respects. While the implanted device may automatically evaluate the patient's state or symptom severity the subsequent automatic operations may not always be desired. For these, and other reasons, fully automatic methods for adjustment or provision of treatment can be less desirable than semi-automatic methods which request a patient's approval prior to performing certain operations. By automatically alerting the patient to a proposed change in the treatment, the implantable device of the current invention offers advantages over both fully automatic, and patient initiated, non-interactive, methods.

An automatic alerting method provides significant advantage since it can provide treatment which anticipates a future need, symptom of the disorder, or patient state. Although a patient may not need therapy at a particular time as may be indicated by evaluation of sensed data, initiating stimulation prior to the need arising can act to attenuate or prevent manifestation of an unwanted symptom. For example, initiating gastrological treatment at a time that is an hour before when the patient normally eats can deter an unwanted event that may normally occur during eating, however, there is no need to do this if on that particular day the patient does not intend to eat, or to eat at a usual time. In this case, relying upon sensed data to adjust stimulation will likely not provide stimulation to treat the event until its manifestation, while stimulation which is suggested according to a time of day or time since last eating may improve therapeutic benefit. The current invention therefore uses automatic alerting to provide pre-emptive stimulation methods that are an advantage over known approaches. Pre-emptive alert messages include sending an alert signal which includes asking a patient to respond to anticipatory questions, such as, "will you eat in the next half hour?", "do you feed a slight aura?", "do you have a slight headache?", "has your feeling of anxiety increased slightly?". Accordingly to the patient alert algorithm, when these questions are answered in the affirmative (e.g., patient input=accept) the device can provide anticipatory stimulation, such as a stimulation program which slowly begin to stimulate a target that modulations the digestive system in a manner which will assist the subsequent digestion process. Instead of developing complex algorithms to accurately detect slight changes related to the disorder (e.g. a slight increase in anxiety) or symptom onset, the device can use methods which correctly detect these at least, for example, 50% of the time, and can be made accurate by simply automatically sending an alert signal to the patient to confirm or deny a treatment operation that is based upon these changes.

A stimulation system which automatically sends alerts throughout the day, or in the middle of the night, to the patient may provide more accurate therapy but may be unpleasant to the patient. The automatic alerting methods do not necessarily occur for all treatment operations, but can rely upon an alert protocol in which alerts are only send during certain times and only for certain types of operations that are specified by the patient. These operations can be, for example, adjusting a stimulation parameter in a manner which may produce unwanted side-effects, such as increasing voltage above a specified amount; adjusting the patient state value; resolving two types of contradictory information; and responsively providing stimulation according to selected medical events. In addition to changes in patient state, detection of a medical event can cause the control subsystem 20 to send an alert message 86 before providing responsive stimulation.

The semi-automatic methods for guiding the treatment using automatic alerting include a number of alternative embodiments. The methods can include: alerting the patient to changes; querying the patient about proposed changes that are to be made; sending alerts to obtain patient input information to resolve potentially contradictory information; and alerting in response to a number of other scenarios. In response to the automatically generated alert issued by the system, a patient can provide any number of patient responses and the device 10 must be able to address these different possibilities. These semi-automatic protocol adjustment methods are shown in the embodiment of FIGS. 6A and 6B, which can be used instead of, or in addition to, the fully automatic methods, such as that shown in FIG. 5. It is understood that the patient, doctor, or treatment program can toggle the system to work in a fully automatic mode, a semi-automatic mode, or a manual mode where the patient determines the characteristics of the treatment protocol implemented by the treatment program.

FIG. 6A, illustrates a method of providing semi-automated therapy to a patient which is guided by patient input provided in response to automatically sent alert signals, in this example, the control subsystem 20 of the device 10 determines that an alert event has occurred for which an alert signal should be sent 85 (e.g. this can occur according to the patient alert rules of the patient alert module 304). In step 86, the patient alert module 304 of the control subsystem 20 automatically issues an alert signal using the communication module 316. A number of conditions (determined by patient alert rules) may cause the patient alert module 304 to issue an alert signal in step 86. For example, if the patient state value becomes different than a current patient state value and indicates a change in the therapy program is needed. The patient state algorithm may use the patient state rules to instruct that this action occur based upon the change in patient state. Alternatively, step 85 may occur if the patient state algorithm is unable to determine the patient state and has issued a request for information from the patient such as defining the current patient state, or choosing between two or more patient states, or simply providing information which will allow the patient state algorithm to define the patient state (e.g. selecting a priority rule). An alert can also be sent prior to adjusting the stimulation (e.g., increasing voltage by 1 volt) or responsively providing stimulation. The alert can be accompanied by a suggested operation which is scheduled to be executed. For example, the system 10 can send the following alert message to the external stimulator, "protocol=sleep, delay=1.5 hours, duration=6 hours?" which means that it will select the sleep protocol in 1.5 hours from present time, and will maintain that protocol for 6 hours. The alert signal can also include a summary of why this decision is being made (e.g. "Time=10 p.m.").

As shown in FIG. 6A, in response to the alert message there are a number of outcomes 88. The patient alert module 304 or control subsystem 20 must be able to function for according to all of these possible outcomes. The patient can either confirm this change (e.g. by pressing a "yes" key on the external programmer or using a magnet to actuate a sensor on an implanted device according to a "yes" pattern which is different than a "no" pattern) 88a, or can confirm a change after modifying a value of the change 88b. For example, the patient can increase the duration of the sleep protocol to 8 hours in the case where it is a Saturday night and the patient wishes to sleep late Sunday morning. Further, the patient can delay this change by an additional amount 88b. Alternatively, the proposed change can be rejected by the implantee 88c. If the implantee accepts the change 88a, or adjusts the change 88b, then the treatment program is adjusted accordingly 90a, 90b. If the patient rejects the change 88c, then the treatment is normally not altered 90c, although what occurs exactly in 90c depends upon the "patient reject" patient response rules implemented by the treatment program. In the case where the patient neither confirms nor rejects the alert message 88d, then the change suggested in the alert message can either by automatically accepted or rejected based upon the patient alert rules for the alert event, as can be defined in a default mode that can reflect the patient's preference. If a patient does not respond, the "no response" rules may operate in a manner that assumes that an alert message was missed (e.g. a send alert rule can dictate that a blinking light may be activated on the external patient programmer). The reliance upon automatically generated alert messages is advantageous since it is a semi-automatic compromise between purely manual adjustment methods and fully automatic adjustment methods, the latter of which may not occur in line with patient needs or wishes.

The method of FIG. 6A illustrates an exemplary method in which an implantable stimulation system 10 semi-automatically adjusts a treatment with the assistance of patient input. The first step is to automatically determine that an alert should occur. The next step is to alert the patient 86. The next step is to wait for a response from the patient. This is referred to as waiting for a "response condition" to be evaluated as true, where the program waits a selected amount of time for the patient to provide a response 88 (which may be set to zero seconds if no delay is to occur). There are two alternatives that can occur in response to an alert signal. If the patient responds 88a, 88b, 88c then the therapy occurs according to the patient input 90a-99c. If the patient does't respond 88d then after a selected time interval a proposed operation will either occur or not occur, according to the patient response rules of the treatment program 92. As shown in FIG. 6B, the response condition is set to false until the patient inputs a response 89a or until a time period expires if the patient doesn't make a response 89b or if sensed data reach some specified criteria. In this example the patient response rule for event alert signal indicates that either patient input, expiration of time, or sensed data exceeding a "cancel alert" criterion will cause the response condition to be evaluated as true and cause steps 89a or 89b to occur. When a patient fails to make a response then the treatment can occur according to "no response" rules 92. If the "no response" rule implements a preference for an event to occur if the patient doesn't respond within a given window then the proposed adjustment may occur in step 92. If the response condition remains false because the time of expiration has been set to a very large value, then the system can simultaneously continue its operation according to patient response rule preferences set by the patient or physician with respect to different alert messages. Further, the response condition can be set to true if during the waiting period, the device determines that there has been another change in patient state (using a "transition" patient alert rule), or other change has occurred, which causes the original alert signal to no longer be valid.

The control subsystem 20 according to the invention sends alert signals, or refrains from sending alert signals, in particular manners according to the send alert rules of the patient alert module 304. The alert module may operate according to an alert protocol that ensures that the alert signal is either repeated or not repeated, in a particular manner while waiting for a patient to respond. For example, if an alert signal was recently sent, then the subsystem can use a send alert rule that prevents another alert signal from being sent to a patient until after a specified delay. This will deter the system 10 from sending repeated alerts, as might occur if the patient rejects a proposed adjustment in the treatment protocol, and the alert event that triggered the alert persists for some time. The patient can not only delay the actuation of a proposed adjustment in treatment for some selected period, the patient can also determine a period during which a treatment protocol can slowly transition from one protocol to another so as not to cause an adjustment that too rapidly for the patient.

The following events, among numerous others, can be defined as alert events which act to trigger alert signals 85: the measurement and evaluation of sensed data; detection of an unwanted medical event; failure of sensed data to meet a criterion; a predefined time-point matching the current clock time information; a relative time-period having elapsed; and, a change in patient state. Some events that can usefully be defined as "alert events" are events that potentially would: result in adjustments to the treatment protocol; result in delivery of stimulation; or perform an operation which would be assisted by input from the patient. Some examples of times that might cause a change in patient state and/or stimulation to be adjusted are: time since an event (e.g., last eating); cumulative time awake; cumulative time asleep; cumulative time since last voiding of bowel/bladder; cumulative time since last insulin delivery; time when eating normally occurs; time when sleeping normally occurs; time when anxiety normally increases; time when depression normally increases; and, times related to a patient's menstrual cycle.

The adjustments proposed by the alert signal could be anything in the treatment program, however, some illustrative examples are: a proposed adjustment in the treatment protocol which includes turning off or attenuating activity of the stimulation and sensing subsystems; an adjustment to the evaluation protocol (e.g., changing a treatment criterion) a proposed adjustment to the treatment protocol including the magnitude of the adjustment, the duration of the adjustment, the rate of transition to the adjustment, and at least one location at which the adjustment will occur.

An alert signal can be triggered if an alert event is defined as a "treatment benefit" criterion failing to be satisfied, since this indicates that the treatment is not providing benefit successfully in relation to the criterion (e.g. the number of detected medical events is increasing over time). Treatment benefit criteria can be evaluated to produce values indicative of successful or unsuccessful treatment. Other alert events can be defined where unsuccessful treatment occurs if a number of specified medical events are detected within a specified amount of time, or if the number of events per unit of time increases more than a specified amount. An alert signal which is automatically generated due to a treatment benefit criteria value indicating unsuccessful treatment may contain a an indication of what criterion was failed and can also include a proposed adjustment according to the therapy algorithm of the control subsystem 20. For example, if tremor size has increased above a certain level for a specified duration, then an increase in the stimulation voltage compared to what has been previously used may be suggested.

Patient State.

In FIG. 5, the present state of the patient is determined in step 76 using sensed data which is obtained in step 74. It should be noted that step 76 can include a number of methods of evaluating sensed data as is well known such as using a discriminant or other classification equations, pattern matching algorithms, or threshold criteria which can be statistical criteria such as guard-bands and confidence limits. The determination of patient state can also be accomplished by comparing the currently sensed data of a patient to past patient sensed data (e.g., using a self norm). In this manner, present state is not necessarily defined as a particular state, in and of itself, but is rather defined as simply different from a previous state, and can be defined in relation to that state. The change between the current state and the previous state can determine the type of treatment adjustment which occurs, as is dictated by the rules implemented by the patient state algorithm of the patient state module 314. However, regardless of the method used to define patient state or detect changes in patient state, the method can include a step in which the change is defined as an alert event and the device automatically issues an alert message to the patient to attempt to gain the patient's assistance in directing treatment by providing patient input in response to the alert.

FIG. 7 and FIG. 8 show two alternative embodiments which generally demonstrate that a patient state can be calculated using sensed data information which is then used to adjust treatment. The method of FIG. 7 utilizes a change in patient state, rather than the patient state value itself, in order to determine how treatment will be adjusted. Rather than a patient state being defined as "running", "sitting" etc, the method only utilizes a difference between a current state and a reference state, according to one or more patient state criteria of the patient state module 314. If a change has occurred, the program may adjust treatment according to rules of the patient state algorithm. As is shown in FIG. 7, the sensed data are collected 100 for a specified duration, such as a 5-minute window, and are processed to provide reference state data 102. A reference state may be statistically defined by processing the sensed data using the processing module 306 to obtain a mean and standard deviation or may be otherwise defined in a statistical or non-statistical manner. New sets of sensed data are then subsequently collected 104, and are processed to define a present state 106. The present state is then compared to the reference state 108, and the comparison determines the present state to be either the same 110 or different 112 than the reference state. For example, if a measurement of the present state data 106 data is more than 2 standard deviations from that measurement in reference state data 102 then a change of state can statistically defined as having occurred at about the $p<0.05$ level. If a change of state has occurred according to the criteria defined in the patient state algorithm of the control subsystem 20, then a new treatment protocol can be selected in a pre-determined manner according to patient state rules. For example, a parameter value of the stimulation protocol can be increased proportionately based upon a characteristic of the present state increasing relative to the reference state. The treatment program may cause the reference state to be updated in step 115 according to the treatment protocol. For example, after a number of iterations of the process have occurred, after a certain amount of time has elapsed, or based upon a criterion such as the present state of the last process being different than the reference state. When the step 115 results in a "true" result then reference data are again sensed 100, while a "false" result causes this step to be skipped and the routine reverts to step 104. Automatically sending an alert message may occur between, for example, step 112 and 114, by performing approximately the method of FIG. 6A.

Alternatively, rather then using change criteria, patient state can be derived from the sensed data by classification of this data. In FIG. 8 classification of a patient's state can automatically guide the selection of protocols. In one embodiment; the process can start at step 104 where data are sensed to derive the present state. After the data are processed 106, the present state is compared to a database of reference states which were previously defined (e.g. in steps 100, 102) or which is defined occasionally when step 115 is set to true, and the protocols (e.g. stimulation, evaluation, and/or sensing protocols) are chosen based upon a classification of the present state 113. For example, the present state can be classified as one of the reference states that the present state most closely approximates, where each of the reference states is associated with a specified protocol. The classification of the present state into one of two or more reference states can occur using a number of classification strategies as is known. For example, sensed date may be submitted to a template matching or discriminant algorithm in which class membership (classification of the present state as one of the reference states) is determined by the group to which the highest probability score is assigned. The protocol associate with the classification is then selected 116, and used to provide treatment 118. It is clear that the methods of FIG. 7 and FIG. 8 can be used in a system which also defines patient state based upon time information by inserting these methods, with slight modification, into the method of FIG. 5. For example, rather than step 118 of FIG. 8 occurring step 78 of FIG. 5 can be invoked. These and other methods of treatment can be used to adjust the stimulation protocol and can also be used with the methods described in the next section which adjust the sensing and evaluation protocols.

Lastly, it should be noted that methods that use patient state values can be applied to systems which use a plurality of stimulation devices. For example, rather than simply turning a stimulator on or off, when more than one stimulator is used, the methods performed may leverage this configuration to provide improved therapy. In one method during stimulation which occurs with more than one stimulator (e.g., bilateral stimulation) the stimulation can be turned off in an alternating manner with respect to the multiple devices. For example, a brain stimulation protocol for each hemisphere of a patient's brain can cycle in approximately a 24 hour period rather than the 12 hour period usually used so that stimulation is turned off to each hemisphere every other night. Alternatively, the two stimulators can switch from "on" to "off", every hour, in an alternating manner so that one of the stimulators is always on. In order to ensure that the clock times of the two stimulators are synchronized, and compensate for any error in synchronization, this type of cycling by a network of neurostimulators can be coordinated by an external patient programmer. These methods decreases energy usage and also address issues such as adaptation when providing neurostimulation. Further, the methods incorporating patient state can be applied uniquely within each stimulator, or data pooled from all stimulators can be utilized by the method in the determination of patient state.

Adjusting Sensing and Evaluation Protocols.

It will be noted that a number of advantages can be obtained by shutting off or adjusting the evaluation and sensing protocols as well as, or instead of stimulation protocols. However, known systems and methods only halt the application of therapy and tend to ignore the operations related to sensing and evaluation of data. Generally, evaluation protocols are not modified in order to change the types of events that are detected. For example, in known approaches, thresholds used by an evaluation program to detect an electrophysiological signature of tremor or pain are not changed due to patient state (e.g., increased during sleep).

In one embodiment, a system according to the current invention is be capable of adjusting the sensing and evaluation protocols (e.g. locations, rate of occurrence, or duration) rather than only adjusting the stimulation protocol. In FIG. 5, rather than simply halting or otherwise adjusting the stimulation of the device, patient state can be used to adjust the sensing and evaluation protocols in step 82. By altering the evaluation protocols at different times, different types of detected medical events can lead to stimulation treatment, and thereby provide improved and appropriate therapy. Two or more protocols that may be selected based upon time of day, may utilize different treatment criteria to provide treatment for different symptom characteristics during different patient states.

In the current invention, the evaluation protocol, which is used to evaluate the sensed data, may be adjusted based upon patient state (e.g., steps 114 and 116 of FIG. 8). Tremor magnitude, such as power within a frequency range that corresponds to the primary oscillations of the tremor, and the treatment criterion used by the evaluation protocol of the treatment program can dictate that if the tremor magnitude is greater than a first specified threshold that stimulation should occur. If the patient state indicates that the patient may be sleeping then the treatment criterion may be adjusted so that a second threshold is used, which is larger than the first threshold. Patient state can be used to cause responsive stimulation to occur in response to events which exceed a second threshold (e.g., only larger tremors, which could awake the patient will result in responsive stimulation the patient is sleeping). When a sleeping evaluation protocol is used, the treatment criterion used to detect a sufficiently large tremor may be set by automatically sending an alert, prior to the patient falling asleep, which requests that the patient specify the $2^{nd}$ higher threshold which is to be used. If the patient experienced increased symptoms during that particular day, the patient may decide to set the $2^{nd}$ higher threshold lower, or higher, than what is normally used, according to the previous experiences of the patient.

The type of sensing, duration of sensing, rate of sensing, or other parameter which guides the sensing protocol can be adjusted based upon patient state. For example, when the patient is sleeping the sensing duration can be decreased by a clinically or operationally significant amount, e.g. by 30% or more of what is normally used when the patient is awake. Additionally, because the sensed data must be processed and evaluated, decreasing the sensing operations will also result in less energy being used to process the sensed data and extract the relevant features that are used to provide treatment.

During therapy, there are periods when data should not be sensed, or at least sensed data should not be evaluated, such as during physical activity when large muscle activity can interfere with the accurate sensing of the data. If earlier processing of the sensed data indicates a patient state in which data should not be evaluated, then more complex evaluation routines may be halted. This is different than allowing the instrument to process the data, and then simply ignoring the results in the case where, for example, EMG activity is overwhelmingly confounded by extrinsic or otherwise irrelevant factors (such as artifact and noise), thereby preventing the processed data from being sensibly evaluated. Further, in some instances, sensed data should not be collected during certain times. For example, sensed data can be used to compare the efficacy of two protocols, as could occur in order to select the protocol that provides improved suppression of symptoms. In this instance, the sensed data should be collected and evaluated only when the patient is in a similar state (e.g. awake and relaxed in both states). In one embodiment, the performance of at least 2 stimulation protocols is evaluated, wherein the sensing and evaluation during a second state only occurs when the patient is in a similar state to a first state, and the first state occurring during a period when a patient state meets specified criteria which are defined to provide an accurate estimate of therapeutic efficacy. In order to decrease variability of sensed data that is unrelated to the efficacy of a treatment, sensing and evaluation can occur only when patient state information indicates that a patient is in a desired state, e.g., relaxed, sleeping, or even in a particular sleep stage. Accordingly, in FIG. 8 steps 15, 100, or 104 may be delayed, or adjusted, based upon sensed data or a patient state value, in accordance with this principle.

One way to reduce the number of stimulation permutations which are potentially used, and to improve therapeutic benefit is to have a default program which is conditionally changed as in the '286 patent application. Another method is to associate different sets of stimulation protocols with different sets of sensing protocols so that stimulation protocols which are possibly available are determined based upon the sensing or evaluation protocols that are chosen. The pairing of sensing, evaluation, and stimulation protocols using "S-EV-S set" rules is a feature of the present invention. For example, if the evaluation protocol used in the sleeping protocol is designed to only detect large tremors, which surpass a second higher threshold, then stimulating with a protocol designed for smaller tremors will cause an unnecessary delay in treatment. For example, using a protocol which is normally used when the patient is awake, the device could evaluate the first ("smaller voltage") treatment as unsuccessful prior to adjusting treatment (e.g. increasing voltage). Since the evaluation protocol which is selected is designed to detect larger tremors, the stimulation protocol with which it is paired according to S-EV-S set rules, can be designed for the types of medical events which will be detected. Analogously, when treatment signals are generated using control laws, the parameters of the control law algorithms can be implemented to realize the principles of the S-EV-S set rules.

Further, the current invention can use dynamic threshold criteria that utilize different thresholds according to patient state values (e.g. during different points of the day). A patient may experience the same amount of tremor, pain, or anxiety as more undesirable in the morning and more tolerable during later parts of the day. If sensed data are used to responsively provide treatment for these symptoms throughout the day using the same threshold criteria then the patient will have to re-adjust the treatment protocol more intermittently then if the threshold criteria change according to the time of day. Further, in the current invention the sensing protocol can be changed so that different measures of the sensed activity are obtained and evaluated in different states. Accordingly, a first set of measures are derived in the "awake" patient state and compared to an independent set of criteria, and a second set of measures are derived in the "asleep" state and compared to an independent set of criteria, and the first and second set of measures may be at least partially independent. This method is unique from simply changing the threshold criteria, and may be more sensitive to some medical conditions. It should be reinforced, here and elsewhere in systems according to the invention, that threshold and other criteria need not be static values or metrics, but may be dynamic and dependent on time, patient state values, and other measures subject to measurement or calculation.

Treatment, Treatment Facilitation, and Symptom Relief.

Known devices deactivate or halt stimulation during sleep, mainly with the goal of decreasing power usage and habituation effects. While it is noted that acute cessation of stimulation can lead to unwanted effects, such as the re-emergence of symptoms, this problem is not addressed in known systems. For example, turning the stimulator off during sleep can permit elevated symptom levels to return in disorders of pain, anxiety, tremor, or headache and could cause a sleeping patient to awake or may disrupt normal sleep architecture. In psychiatric disorders, there may be a lag period between the time that stimulation is initiated and when the desired therapeutic benefit is obtained. Due to these concerns it is sometimes advantages to decrease or otherwise alter stimulation, rather than fully halting it.

In one method of the current invention a parameter of the stimulation protocol is decreased a relatively large amount in order to decrease power or drug consumption, while still providing for stimulation which is sufficient to avoid unwanted effects which would be caused by complete cessation of stimulation. When two or more stimulation protocols are provided, at least one stimulation protocol is characterized by a clinically or operationally significant amount, such as a relative decrease of at least 30% for at least one parameter. The parameter may relate to voltage level, number of sites at which stimulation occurs, or duration of stimulation over a given period.

Alternatively, the protocols selected during a particular patient state, such as asleep, may not always utilize less power, but rather, may simply be oriented towards providing a different type of treatment goal than in a different state such as the awake state. For example, while the awake protocol can address relief from symptoms, the sleep protocol can be oriented to treating the disorder itself such as increasing a particular type of neuronal firing that is therapeutic in an indirect manner. In this case, a first stimulation protocol is used which directly deters or decreases symptoms of a disorder, and a second stimulation protocol is used which provides a secondary benefit or has a secondary goal. More generally treatment includes providing therapy according to a primary treatment goal when the patient is in one state and a secondary treatment goad when the patient is in a different state. A secondary benefit may be one of the following: a benefit which is indirectly related to the symptoms of the disorder; a benefit which promotes neuronal repair of damage caused by the disorder; a benefit which is facilitating therapy that will be provided at a later time to provide symptom relief; a benefit which is to produce a change in neurotransmitter levels in a manner that facilitates subsequent therapy and a benefit which promotes treatment by the first stimulation protocol. A primary and secondary treatment protocol can be configured to achieve two different goals, or may be otherwise oriented.

Certain types of stimulation have been shown in scientific literature to modulate neurotransmitter levels in both near and distal sites from stimulation, and to assist in neuronal repair. Hence, the secondary type of stimulation may be directed towards long term treatment by modulating neurotransmitter levels, or cellular activity, which are related more to the treatment of the disorder itself rather than to simply providing acute relief of a particular symptom. Because the electrical activity of the brain is directly related to its neurochemistry, electrical neuromodulation can alter the biochemical substrates of brain activity, and modulators of this activity, such as neurotransmitter levels, extracellular levels of GABA and glutamate, and ions such as calcium and potassium (Windels, et al 2003, Graham-Jones et al, 1985). These modulations can, in turn, induce various changes in the membranes of the neurons as well as intracellular processes. Target neuronal tissue can be more greatly affected by stimulation when the chemical characteristics of the tissue are within certain ranges, including the amount of ions available in the extracellular fluid. The secondary treatment goals can modify the electrical, metabolic, cellular, molecular or neurochemical profile of brain regions in a manner which has a different treatment goal than that of the first protocol.

Certain types of unwanted endogenous activity, such as seizures, firing in a certain manner such as a burst or non-burst mode, firing of certain regions, or types of cells, may only occur when levels of chemicals in the extracellular fluid, including levels of one or more transmitters, in one or more regions, are within a certain range (e.g., Velisek et al, 1994). Rather than responsively stimulating in response to the emergence of unwanted types of activity, preventive stimulation modulates the system in order to decrease the risk that these events will arise in the future. Stimulation can occur during patient states such as sleep which can deter the levels of transmitters from exceeding the desired ranges during the subsequent waking state, which, in turn, may cause subsequent neurostimulation oriented towards blocking seizures to be more successful. In one embodiment, a first neurostimulation protocol is used to produce a desired change in neurochemical levels, and second neurostimulation protocol is used to provide responsive treatment for a disorder, such as responding to epileptiform activity, and these two protocols are selected based upon the state of the patient. In another example, when used to treat a disorder such as gastroparesis, one stimulation protocol can be used during or proximate to food intake to modulate stomach emptying, while another stimulation protocol is used periodically simply to strengthen stomach muscles or provide other desired effect. Accordingly, treatment goals can be altered based upon patient state to achieve a primary treatment goad and a secondary treatment goal during different states.

Hierarchical Treatment Strategies.

Hierarchical treatment strategies are another feature that may be implemented by the system according to the invention. Generally, hierarchical treatment strategies can be accomplished in a serial manner, where the outcomes of lower levels determine whether higher level operations occur, and if so which operations these may be. One type of hierarchical strategy which has already been discussed is that use of patient alerts, where the automatic generation of the alert may be considered a lower level operation, which then leads to subsequent operations based upon the patient's response (or lack thereof). In a general embodiment; the hierarchical strategy uses lower level operations until at least one "level criterion" is satisfied, which permits operations at higher levels to occur. Movement from lower to higher levels can utilize level criteria such as: a threshold criterion; a treatment benefit criterion; a change in patient state; or, the detection of an event which is not able to be classified with current sensed data. A number of other multi-stage strategies can provide advantages as well, some of which will now be described according to the current invention.

Known methods describe utilizing sensed data as may be obtained from multiple sensors and which may include multiple sensing modalities such as electrical, optical, and chemical. These different types of data may all be used to define patient state or to identify an unwanted medical event in order to responsively provide treatment. Normally different measures of sensed data can be utilized in combination by applying unique threshold criteria to each of the measures which are sensed, where if a set of one or more threshold criteria are surpassed then some type of action occurs. Further, the assessment of different measures may be combined using a multivariate equation, or using an algorithm having compound logical operators such as "and", "not", "<", and others that will be apparent to those skilled in the art. These methods allow the multiple measures of sensed data to all contribute to the determination of patient state or identification of medical event and are examples of parallel evaluation of sensed data derived from a plurality of sources.

While some advantages of using patient state to adjust the sensing and evaluation protocols have already been discussed, it is an advantage of the methods of the current invention to utilize an alternative embodiment of this method whereby operations and protocols, such as sensing protocols, are performed serially in a hierarchical fashion. Serial methods have advantages over methods that assess all information essentially in parallel, and "hierarchical" analysis of data can especially provide a number of advantages over the strictly parallel approach. For example, in the case where multiple sensors are available in the implanted system, continuous sensing and evaluation from multiple sources will require more memory in the implanted device as well as processing resources and will utilize more power. Some sensors require more energy than others and this fact should be capitalized on by hierarchical based methods. An EEG amplifier may sense electrical data in a lower level sensing protocol and only when medical events are detected, and this detection is defined as a level criterion, does an additional sensor, which may be an optical sensor that may require more energy over time, become activated in order to obtain additional information, for example, information related to bloodflow. In another instance, when using neurostimulation to treat a depressed patient, the detection of theta power in a specific region of the brain may only lead to responsive neuromodulation when levels of serotonin in that area are simultaneously below a specific level. In a exemplary implementation, serotonin is not sensed, or at least assessed until the theta power exceeds a level criteria. This is different than a simple combination criteria with two operators combined with an "and" condition. In this case the second operation does not occur until the first meets a level criterion. Accordingly, while neurophysiological measures and neurochemical measures may be combined (e.g. using a model, multivariate equation, or by parallel/sequential logic) in an assessment of a neurological event, the biological (neurological) context within which can event occurs, and in determining whether stimulation should occur or be adjusted; the measures of the second modality are not sensed unless there is a chance of the cross-modal measurement (e.g., a chemical/electrical ratio utilizing multiplication by constants to relate the two measure in a sensible context) meeting some treatment criterion. By sensing according to a first sensing protocol, from a first subset of sensors, and switching to a second sensing protocol, of a second subset of sensors according to hierarchical rules the device can save power and accomplish adequate sensing with less resources. For example, in the case where medical events are not occurring there may be no need to obtain information from, or analyze data from, all available sensors. Alternatively, if a threshold is exceeded and a medical event may be occurring then data from additional sensors can be sensed and analyzed in order to obtain more information and provide data for which additional criteria can be applied.

In addition to sensing, processing and evaluation of sensed data can also occur using multiple levels, where more extensive analysis occurs only when the analysis from a lower level indicates indicate that this is necessary. Multi-level operations may also be used for the stimulation protocols, as well as for all treatment operations related to a particular protocol or across different types of protocols. For example, when the evaluation of sensed data at a lower level indicate that a medical event has occurred, and stimulation occurs in response to this event, then afterwards data may be sensed more comprehensively. Just as sensing can occur in a serial manner utilizing a multi-level design, and proceed from lower to higher levels when, for example, threshold criteria are not met, the movement from a lower to a higher level can be interleaved with changes to the stimulation and evaluation, protocols.

Figure 9:
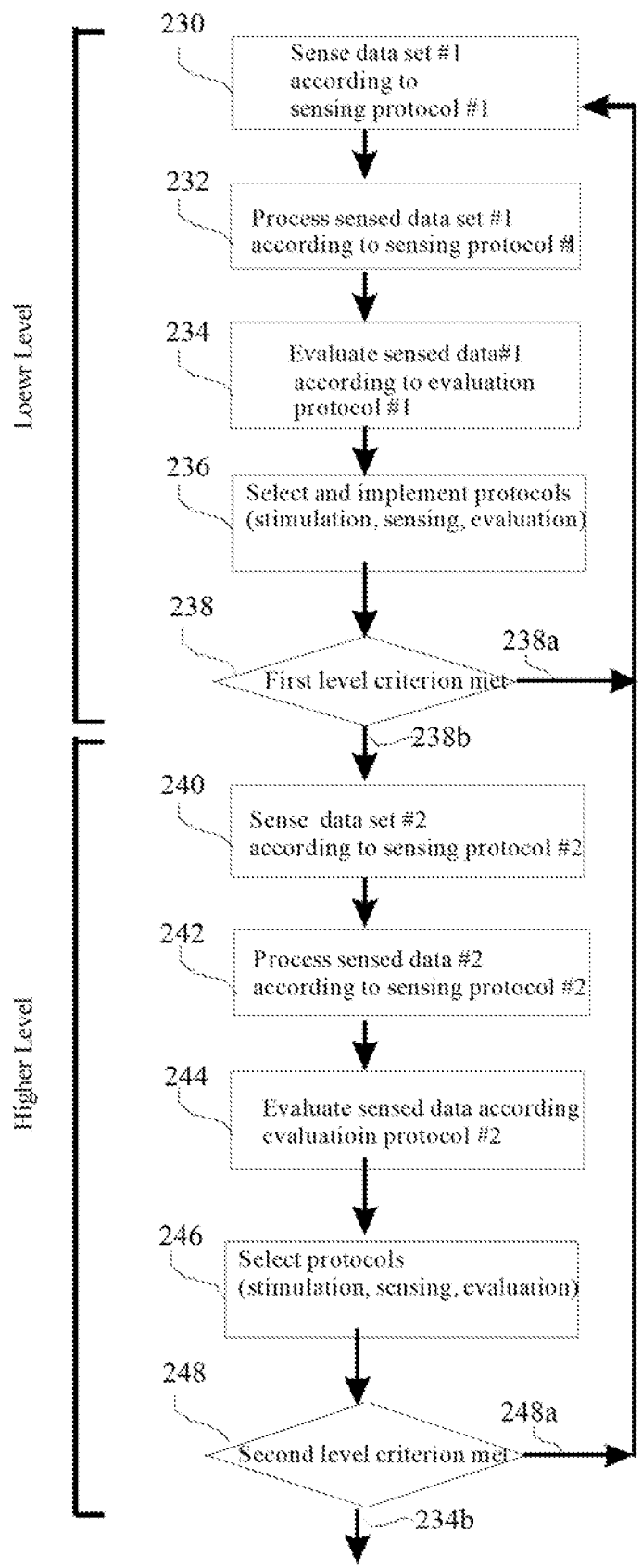
FIG. 9 shows a schematic representation of a serially-implemented hierarchical method for evaluating sensed data and providing therapy using level criteria.

FIG. 9 shows an embodiment of a multi-level method which can be used to combine simple and more complex methods of sensing (and evaluation), respectively, in lower and higher stages of an algorithm, and which can be generalized to a wide number of situations. Although only sensing and evaluation protocols are shown, in the figure, stimulation protocols can be utilized as well or instead. For example, the method can be generalized to combine the sensing and evaluation of a plurality of data in a sequential fashion. Alternatively, the method can use a first type of protocol before an event is detected, and different one after an event is detected. The treatment method can also oscillate between a single and a multi-level analysis. The alternation between these two types of analysis may be made contingent upon the detection of, for example, alert events, patient input, and selected patient states, when these are defined for level criteria.

In step 230 of FIG. 9, sensed data are obtained according to a first sensing protocol. The sensed data are related to at least one measure of the patient as may be sensed by a particular type (e.g., electrical or chemical) of sensor. According to a first protocol, these data are processed 232 and evaluated 234. The evaluation 234 can consist of processing the data to obtain measurements which are compared to a first treatment criterion, in step 236 the protocols are selected according to the evaluation 234 and the next stage of the serial multi-level algorithm does not occur 238a unless a level criterion is met. In step 236 if a stimulation protocol dictates that stimulation should occur then this is done. If the first level criterion is not met 238a, then the algorithm returns to step 230 where and more data are again sensed according to a first protocol. If the level criterion is met 236b then the next higher level of the multi-level algorithm occurs. If more data are required then step 240 occurs where more sensed data are obtained according to a second protocol. This second data set is then also analyzed according to a second protocol which is selected and/or adjusted based upon the first level criterion being met. For example, if evaluation of the first sensed data (which was achieved by comparing this data to an epileptiform activity template) indicated that an unwanted medical event was occurring, and caused the first level criterion to be met (the first criterion is met because it stipulates that this type of activity must occur, although the logic can be arbitrarily switched using a logical operation in the comparison, as is well known), then the second protocol can adjusted or selected based upon characteristics of this failure 238. In this manner, the sensing and evaluation of sensed data 242, 244, (or the stimulation treatment in an alternative embodiment), can be adjusted to be specific for the type of event that was detected.

The same signal or data can be iteratively processed using more complex algorithms, when the algorithms in earlier levels indicate further processing is needed (e.g. level criteria are met). One example may include a method where EMG tremor only results in stimulation when a cardiac or other measure indicates the patient is resting or not engaged in physical activity. The EMG data which is processed to detect muscle activity, can also be filtered and processed during a second level of processing in order to also measure the patient's EKG and its related measures such as inter-beat interval. Although the adjustment or selection of any of the protocols of the treatment program can occur at any step of the method according to rules defined in the treatment program, the embodiment shown in FIG. 9, explicitly shows step 238 which reflects that treatment protocols can be adjusted in a multi-level manner to provide serial processing according to results of sensed data, or for other reasons, during the course of treatment. In step 246 if the second level criterion is not met 246a then the process reverts to step 230. However if this latter criterion is met as well 246b, further levels of sensing and evaluation will occur.

The hierarchical method is shown in a simplified embodiment in FIG. 10A, wherein a first treatment protocol is implemented 260, unless a first-level criterion is met (or exceeded 262b, depending upon logic of first-level criterion 262. If the criterion is met 262b then the treatment program utilizes a second (higher level) treatment protocol 264, otherwise it reverts 262a to the first treatment protocol 260. In some instances the implementation of the higher level protocol can occur jointly with the continued operation of the first protocol. While the second treatment protocol is active, if a second-level criterion 264 is met 266b then the treatment program may utilize a third treatment protocol (and so forth, as indicated in the illustration). Otherwise, if the second-level criterion is not met 266a the program will either continue with the second treatment protocol 264 or will return to the first treatment protocol 260, depending upon return path rules and criteria which are assessed in step 268. Return path rules and criteria are used to allow the treatment program to determine path flow. For example, whether certain which steps should be invoked if a level criterion is not met. The first treatment protocol 260 can include automatically sending out patient alert signals according to an alert protocol. Calculating the first-level criterion 262 may also utilize an alert protocol in order to enable a patient to assist in determining if criteria have been met. In FIG. 10A the "(if)" statements indicated that the control subsystem may only implement operations if these are indicated by the therapy program.

FIG. 10B extends this approach to a case where a first treatment program provides therapy in the generalized case, and there are several first-level criteria which can be met in order to cause one of several second-level treatment protocols 264a, 264c, 264d, to be implemented. The different second-level treatment protocols are customizable to detect, evaluate, classify, and adjust and provide treatment according to different types of detected medical events or patient state or both. The treatment program can utilize priority rules in order to select an applicable second-level treatment protocol. For example, if one set of second-level criteria require that conditions A and B are both true, while a different set of second-level criteria require that conditions A and B and C are all true, then this latter set of second-level criteria might be assigned priority, since it is more specific. In other words, level criteria can be constrained by priority rules so that when multiple level criteria are met, one level criterion has priority over the others, so that the subsequent operation occurs according to this priority. Selection of one or more higher level operations, when using multiple level criteria, according to other methods are possible. Additionally, multiple higher level operations can occur simultaneously when multiple level criteria are met.

Figure 11B:
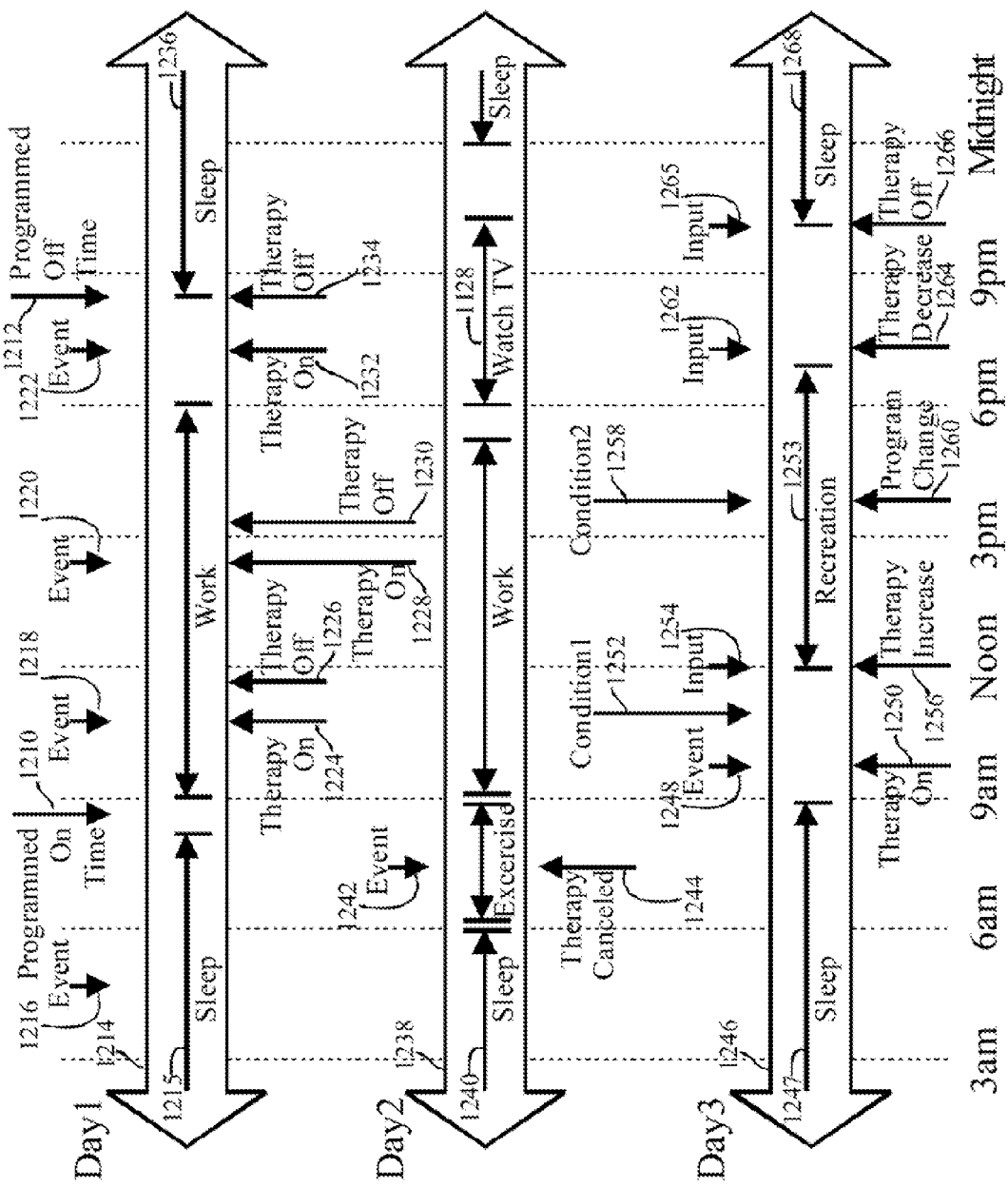
FIG. 11B is an exemplary is an exemplary timeline illustrating therapy program modification according to condition changes, detected events, and patient inputs according to the invention; and, FIG. 12 is a schematic representation illustrating the external patient programmer according to an embodiment of the present invention.

Two illustrative scenarios in the use of systems and methods according to the invention are set forth in FIGS. 11A-11B. Referring now to FIG. 11A, an illustrative timeline scenario is presented in which an embodiment of the invention is operative to control therapy delivery according to the time of day and the patient's inputs. For purposes of this example, the patient suffers from tremor, and the device 10a is programmed to initiate therapy at a programmed "on time" 1110 of shortly before 9:00 a.m. and to end therapy at a programmed "off time" 1112 of shortly before 9:00 p.m.

On a first day 1114, the patient sleeps 1115 until shortly before the programmed "on time" 1110, and accordingly, shortly before the programmed "on time" 1110, the device 10a provides a notice to the patient (by way of an audio or other alert signal (generated by the device 10a or its programmer 400, for example). To prevent the routine alert signal (i.e., the therapy-on request) from disturbing the patient, a silent alert, such as a blinking light on a patient programmer) may be provided that will be noticed upon awakening. In the example, because the patient is awake, the patient accepts the "activate therapy" operation suggested by the alert signal. For example, the patient can wave a magnet twice over the device 10a, or can interact with the programmer 400 and cause the programmer 400 to communicate the confirmation to the device 10a), and therapy is activated 1116 according to the patient response rules, at the programmed on time 1110.

Later on the first day 1114, the patient goes back to sleep 1118 at 9:00 p.m. Shortly before that time, the device 10a or programmer 400 provides a notice to the patient. Again, the notification may be silent to prevent disturbing the patient if already asleep, but it may be different than (e.g., blink in a different pattern or use a different color) the alert signal which signified the "therapy on" notice. In this case, the patient accepts the "therapy off" action prepared by the alert signal (for example, confirmation can occur by waving the magnet twice over the device 10a, or by interacting with the programmer 400), and therapy turns off 1120. In an embodiment of the invention, the request to disable therapy for the day may be confirmed also by ignoring the alert, and after a short delay (of, for example 10 seconds to one hour), therapy is turned off according to a priority rule for the "therapy off" event. The alert system may have a patient alert rule which dictates that is a patient fails to respond to an alert signal, that a unique color is flashed, for some selected duration, indicating that an alert signal was "missed" by the patient, and depending upon the flashing pattern, may also indicate that a decision has been made, or operation has occurred, without the patient's response. The patient can then query the patient programmer to ascertain what actions have occurred without response.

On a second day 1122, the patient only sleeps until 6:00 a.m. 1124, and awakes well before therapy is scheduled to initiate 1110 for the day. Accordingly, to enable therapy and provide relief from the patient's symptoms, the device 10a is adapted to receive a patient input (e.g. one or more magnet swipes or an indication made on the programmer 400) to initiate therapy 1126 before the programmed "on time" 1110. Later, at the programmed "off time" 1112, a "therapy off" alert signal is provided to the patient. Because the patient is watching television 1128 at that time, the patient rejects the request rather than approving it, and either inputs a delay value (a specific later time for the therapy to turn off), rejects the operation and requests re-notification at a later time; or provides a different patient input associated with the rejection of the suggested operation, so that the "turn off therapy" operation occurs at a later time 1130.

On a third day 1132, the patient sleeps until 9:00 a.m. 1134, just past the programmed on time 1110. Accordingly, no approval is made in response to the initial patient alert signal provided by the device 10a or programmer 400, and therapy is not activated until later 1136, when the patient notices the alert and approves the operation suggested by the "therapy on" alert signal. In a different embodiment, a failure to confirm a "therapy on" request can result in the request being canceled and the patient must then remember to turn the device on upon awaking. Alternatively, the failure to confirm can lead to an audio signal, which slowly ramps up in intensity, being added to the visual signal, and other actions may also occur according to the patient alert rules. Later in the day, the patient turns the therapy off 1138 by manually providing patient input to the device 10a or programmer 400. This can cancel a "therapy off" alert signal slated to occur later in the day since the device is already in the off state.

It will be noted that in the scenario illustrated in FIG. 11A, two different priority rules are used by the patient alert module, one for "therapy on" and the other for "therapy off." For therapy on, patient input prevails over time of day—confirmation is required to turn on therapy. For therapy off, time of day prevails—failure to confirm still results in deactivation. The priority rules here are programmed to vary either temporally or according to particular alert events.

Referring now to FIG. 11B, an illustrative timeline scenario is presented in which an embodiment of the invention is operative to activate and deactivate therapy, control the quantity of therapy delivered, and change responsive detection programs according to the time of day, elapsed times, patient inputs, detected events, and sensed conditions, using a hierarchical sensing paradigm as described above. Also for this example, the patient suffers from tremor, and the device 10a is programmed to initiate therapy at a programmed "on time" 1210 of shortly before 9:00 a.m. and to end therapy at a programmed "off time" 1212 of shortly before 9:00 p.m.

On a first day 1214, the patient sleeps 1215 until shortly before the programmed on time 1210, and while sleeping, an event is detected 1216 by the device 10a. In the example under discussion, therapy is enabled only for serious medically relevant events, which are defined as being above a selected magnitude threshold which is higher than is used while the patient is awake, while the patient is sleeping. In this case the detected event 1216 is below the "sleeping threshold" and does not result in any therapy being applied. In this case, the patient state value has been used to adjust the evaluation protocol.

After the programmed "on time" 1210, when therapy is enabled for all detected events which are above a lower first threshold, three events occur during the first day 1214 that are sufficient to result in therapy being applied; a first event 1218, a second event 1220, and a third event 1222. Each detected event is followed by an approximately one-hour-long session of therapy. For the first event 1218, the therapy is automatically turned on 1224, therapy is delivered, and therapy is later automatically turned off 1226. Similarly, for the second event 1220, therapy is turned on 1228 and later off 1230. However, for the third event 1222, in the illustrated embodiment, the time between therapy on 1232 and therapy off 1234 is shortened by the intervening programmed "off" time 1212. This mode of operation may be useful in situations where therapy is disruptive to sleep patterns 1236, and as with the example set forth in FIG. 11A above, an alert signal may be provided to the patient, providing the patient with an opportunity to confirm or reject the premature therapy termination. Such an opportunity to confirm/reject may be made available for any of the mode changes of operations performed in a system according to the invention.

On the second day 1238, after awakening from a sleep state 1240, but before the programmed on time 1210 passes, a serious event 1242 (major tremor episode) is detected, for example by sensing and analyzing EEF, EMG, or accelerometer signals. Ordinarily, serious events would result in therapy being applied, even during sleep states, but at this time the patient is awake, receives an alert from the device 10a prior to therapy being applied, determines that the detection is a false alarm (based on a high activity level during the exercise session) and cancels the therapy 1244. Later that day the patient watches television 1128 and notices the alert signal and decides that stimulation should occur all night, the "turn off" therapy operation of the alert signal is rejected according to the patient response, and the patient alert rules dictate that no further alerts are sent, so that stimulation is not turned off on that particular night and no more alert signals are sent.

On the third day 1246, the patient enables therapy upon awakening from sleep 1247, and later in the day, an event 1248 is detected, leading to therapy being turned on 1240 (upon patient confirmation of an alert signal). While therapy is ongoing, a first condition 1252 (for example, a measured increase in susceptibility to tremor) is detected by the device 10a, which has three consequences in the disclosed embodiment: (a) therapy continues, rather than turning off after an interval; (b) the system enables (through either the device 10a or its programmer 400) the patient to increase therapy further, i.e., by requesting an increased dose; and (c) a second (higher) level of detection, which is ordinarily not operative, is enabled to sense further conditions of distress.

Before beginning a session of recreation 1253, the patient provides input 1254 (e.g., a number of magnet swipes over the device 10a or interaction with the programmer 400) to increase therapy 1256, as described above. During the recreation, a second condition 1258 is detected, causing the device 10a to adjust its therapy settings to a different program 1260 as clinically required (the nature of this program may vary from patient to patient, depending on need). For example, if the second condition indicates that the previous regimen of increased therapy is not effective, a different strategy (e.g., different waveshape or frequency) may be employed. Based on the detection of the first condition 1252 and the second condition 1258, a "cumulative" patient alert rule causes therapy to continue after the recreation 1253 ends, although subsequent patient input 1262 lowers the magnitude 1264 of the stimulation of the second therapy program. Further, because of the detection of the first condition 1252 and the second condition 1258, therapy continues past the programmed off time 1212, until the patient manually deactivates therapy just before going to sleep 1268. It will be noted that the scenario illustrated in FIG. 11B employs a hierarchical sensing strategy as described herein, as the first condition 1252 meets level criteria that allows sensing to begin according to a (higher) protocol which detects the second condition 1258.

The features illustrated in FIGS. 11A-11B and discussed in connection therewith are intended to be exemplary and illustrative only, for a particularly hypothetical patient (which may or may not be reflective of a real-world clinical scenario) and do not limit the scope of the invention. Although the example is illustrated with tremor, many other medical disorders could have been used instead. Various pain disorders could also be detected by EMG information which reflects abnormal muscle tonality of some of those disorders, and other sensors can be used to detect other disorders and symptoms.

External Patient Programmer.

Figure 12:
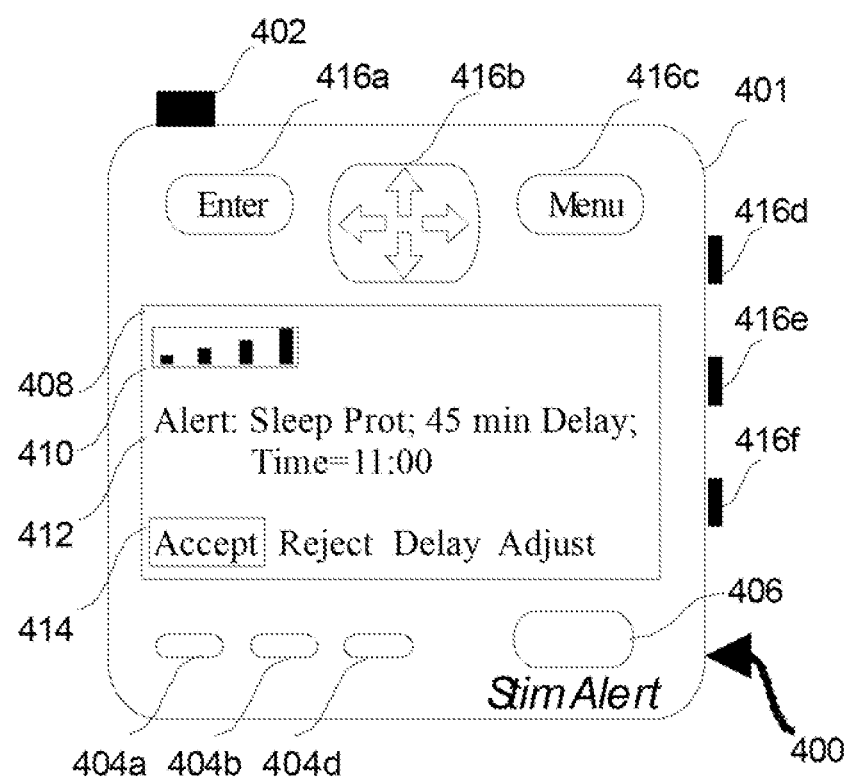

An example of an external patient programmer 400 is shown in FIG. 12 in an embodiment termed "Stimalert". The programmer 400 is contained in a lightweight plastic housing 401 which contains a display screen 408, alert transducers 404 and 406, and control buttons 416 for controlling the programmer and providing patient input responses. The programmer also has communication circuitry, for communicating with the imparted device and/or a computer (which can run a turnkey software program for customizing operation of the programmer and implanted device), which in this example is achieved via a bluetooth transmitter 402. One of the multi-colored indicators 404a, can begin to flash hen an alert signal occurs in the device 10, and is transmitted to the programmer, or is generated within the external programmer 400 itself. If the user doesn't respond within a specified time interval treatment in the device 10 may continue according to patient alert rules which may also cause a different indicator 404b to flash and to notify the user of a missed alert signal. The alert signal may also contain an auditory component which is produced by a speaker 406, or the alert signal can be vibratory and produced by a motor contained within the device 400. The display of the programmer 408 can contain a number of display components including: a bar indicator 410 which indicates transmission strength between the implanted device 10 and the programmer 400; an alert message 410 which, in the example of the figure contains the information about the alert event, including a proposed operation, a selected delay which will be provided prior to the initiation of the operation, and the reason the alert was sent; and, a patient response menu 414 which highlights a default response and waits for the user to confirm this by pressing the "Enter" key 416a. The user may also change the selected patient response using the navigation key 416b, or can invoke other operations or modes of the programmer 400 by pressing the "Menu" key 416c. The device can also contain a number of assignable buttons 416d-f on the side of the housing 401. The assignable buttons can act as quick-keys for performing certain functions. In this example, 416d and 416e can be a volume up and volume down adjustment key, respectively, and 416f can be a "mute" key which immediately halts an alert signal and also rejects or accepts the action proposed by different types of alert signals according to patient alert rules and user preference. The patient programmer 400 is configured to work in collaboration with, and may be conceived as an extension of, the patient alert module 304 of the implanted device. The programmer 400 can implement various alert operations by receiving a simple signal from the implanted device 10, such as a code number associated with performing a predefined alert operation (which is defined in the control subsystem of the external patient programmer that is similar to the control subsystem 20 of the implanted device 10). The programmer 400 can also be configured, according to patient response rules, to automatically send the patient's input back to the device at a time when the implanted device is activated, or can repeat sending the patient's response back until the device receives this information and provides a "communication accepted" response. Methods of successfully communicating between an implanted device and an external patient programmer are well known, and are implemented by the programmer which operates to provide the alert signals according to the methods that have been described herein. The external patient programmer 400 can issue alert signals if it detects that it is out of range, low on power, or if it detects any other situation that will impede its intended function, and which is defined as an alert event.

Further Implementations.

While features of the invention may be especially well suited to be used in the treatment of brain disorders such as epilepsy, pain, and depression these can also be used to treat a vast array of medical disorders of the brain and body. For example, treatment can be provided for psychiatric, mood, movement, cognitive and neurological disorders; seizure and epileptiform disorders; pain disorders; depression, anxiety, phobia-related disorders; cardiac, respiratory and metabolic disorders; disorders of syncope; sleeping disorders; migraine; digestion and voiding disorders, and diabetes. The invention can be particularly beneficial to pain treatment, since halting therapy at unwanted times can cause significant discomfort to a patient. Using patient state information the present invention allows automatic, semi-automatic, and manual adjustment of a protocol prior to, during, or after the time when the patient requires the specified treatment. The implanted devices used in the invention can be, for example, cardiac assist devices including defibrillators, cardioverters, mechanical pumps such as a portable embodiment of mechanical ventricular actuation devices (e.g., Biophan's MYO-VAD) or blood-contacting mechanical pumps (where pumping is understood as a type of stimulation treatment), vagal/cranial nerve stimulators, and spinal stimulators. The implanted devices can also be devices which are primarily monitoring devices which may, or may not, work with other implanted devices to provide modulation of a medical disorder. The implanted devices can be monitoring devices which are used to detect unwanted conditions in, for example, the brain or heart. The implanted devices can be devices for monitoring activity and providing alarms for such conditions as ischemia, stroke, or epilepsy so that the patient can seek help. The implanted devices can be cardiac monitoring devices such as those described in U.S. patent Publications 20050165321, and 20050113705, both to Fischell et al. as well as implanted medical storage devices for collecting records of cardiac or neurological activity. The implanted devices can also be used in medical treatments related biological functions rather than disorders such as modulating processes intended to assist or prevent specific conditions related to contraception, menstruation, weight loss, obesity, and pregnancy.

Treatment for disorders of digestion can include, for example, treatment of disorders of gastrointestinal motility such as gastroparesis (e.g., delayed emptying of stomach contents) and gastroesophageal reflux disease as well as their symptoms (e.g., stomach upset, heartburn, nausea). Electrical stimulation can be used to modulate movement of food through the digestive system and pharmacological stimulation can be used to, for example, modulate the amounts, strengths, and effects of liquids present during direction. Artificial valves, used to treat there disorders, may also be part of an implanted device that is controlled to realize the features of the present invention where stimulation involves modulation of flow. Serotonin receptor agonists, pharmaceutically acceptable salts, or a hydrate or solvate thereof, as well as gastric acid suppressing agents can all be used to provide a therapeutically effective amount of therapy, especially when delivered in relation to food consumption. Stimulation can also be used to therapeutically modulate the volume of gastric juice available to reflux, the potency of the refluxed material, and the interval that the refluxed material remains in the esophagus or other area.

Disorders of breathing, which involve disruption of normal respiratory behaviour, may be a prime candidate for the semi-automatic methods described herein. Breathing disorders are, for example, central apnea, hypopnea, dyspnea, hyperpnea, tachypnea, and periodic breathing. Apnea is a fairly common disorder characterized by periods of interrupted breathing. Central apnea, is one variant, which causes dysregulation of breathing since control signals from the brain to the respiratory muscles are absent or interrupted. While apnea is popularly known as a disorder which is manifested during sleep, it may also occur while the patient is awake. However, the protocols which provide benefit to the patient when awake and asleep are likely to be different and so patient state is particularly important in this type of application. The automatic and semi-automatic adjustment of treatment protocols as has been described herein can include protocols related to activation or de-activation of protocols, and adjustment of protocols related to breathing based upon patient state, where protocols are selected or adjusted based upon, for example, sleep, wakefulness, and activity levels, which may be confirmed using patient alerting.

The following material may provide a general understanding for terms used in this specification, while it is also understood that these terms can be modified, adjusted, and altered within other areas of specification to achieve alternative embodiments of the invention. These definitions are provided for illustrative purposes and shall not be deemed to limit the scope of the invention.

As used herein the terms "stimulation system" or "stimulator" or "device" generally (but not by way of limitation) refer to a system, or part of a system, that is capable of delivery medical stimulation. Stimulation can include modulating tissue by delivering electrical, optical, magnetic, drug or other therapy. The system is comprised of components which are either configured in a distributed manner or are primarily contained within the housing of a single implantable device. A stimulator can be implemented using a generic implantable stimulator or drug pump such as those manufactured by NeuroPace, Medtronic, Johnson & Johnson, Cyberonics, Guidant, and Advanced Neuromodulation Systems, Inc., which can be configured or adapted to provide electrical stimulation according the principles of the current invention. Accordingly, the stimulator 10, can be realized, for example, as either an electrical signal generating stimulator 10a, or a drug pump 10b, or a combination of the two.

As used herein, the term "stimulation conduit" may include one or more leads, each having at least one electrical contact. A stimulation conduit can also be one or more catheters, each of which can be a simple catheter or a combination catheter/lead capable of providing electrical stimulation or sensing in conjunction with drug delivery. Some stimulators may not include stimulation conduits that travel to distal locations from the housing of the stimulator (e.g. BION™), and in this instance the stimulation or sensing probe which resides within or upon the surface of the stimulator may be used identically during treatment.

As used herein, the term "sensor" can refer to a device for measuring an electrical, chemical, optical, or other physical property. A sensor may provide sensed data relating to multiple characteristics, for example, the flow rate, concentration, and pressure of a fluid. A sensor may be an aggregate of multiple specialized components each configured to sense a different characteristic of the environment in which it is located. A sensor may sense, for example, EEG, EKG, ECG, sound, pressure, strain, temperature, perfusion, optical signals, metabolite levels, neurotransmitter levels, cardiovascular measures such as heart or respiration rate, glucose level, oxygen saturation level and other types of information in order to measure state of the patient and to responsively provide therapy. When possible, the invention can rely upon completely implanted sensors, but may also communicate with, external devices, or may utilize information derived from assays, or laboratory techniques, in order to obtain accurate sensed data of the desired measures. In the case of a movement or pain disorder a sensor may be a motion detector or EMG sensor implanted in a limb or can be an EEG sensor located over somatosensory/motor areas of the brain to directly measure features of a disorder (e.g., tremor). When used for digestive or voiding disorders, the sensors can include pressure and strain sensors which gauge the amount of pressure in the bowels, bladder, or any area of the digestive system. The sensor can communicate with and obtain power from the stimulator 10 or can have its own power source may communicate via telemetry. A more comprehensive description of alternative sensor embodiments has previously been made by the inventor in U.S. Application Publication No. 20050277912, entitled "Programmable medical drug delivery systems and methods for delivery of multiple fluids and concentrations".

As used herein, and not by way of limitation, the term "treatment program" generally refers to a program implemented by the control subsystem to provide therapy. The treatment program operates according to a treatment protocol. The treatment protocol determines the stimulation, sensing, and evaluation protocols as well as the parameter values used in these protocols. The treatment program determines, if, how, why, and when the protocols are altered and treatment is provided. The treatment program can be implemented as a software program by the control subsystem, or as specialized hardware within the control subsystem 20, for providing control of treatment.

The term "treatment" generally refers at least to operating to provide therapy or performing an action that is medically therapeutic to the patient. For example, treatment can refer to decreasing or deterring one or more unwanted symptoms of a disorder, which can be medical events. Treatment can also refer to providing stimulation that decreases the likelihood of the emergence of unwanted events.

As used herein, "control subsystem" generally refers to a subsystem that provides control of the treatment according to a treatment program.

An "operating" is a defined as implementing an algorithm for performing actions according to an embodiment of the invention, which may include (but shall not be limited to) stimulation protocols, detection protocols, evaluation protocols.

As used herein "stimulation subsystem" generally refers to a subsystem that provides stimulation, via at least one stimulation conduit, according to the parameters of a stimulation protocol. The stimulation protocol determines where, when, and how to stimulate with, for example, one or more types of stimulation. Not only the type of stimulation but also the number and location of sites at which stimulation can occur are defined by the stimulation protocols. A stimulation parameter can determine each characteristic of a stimulation protocol, such as level of stimulation (e.g., voltage or current), amount of stimulation (e.g., duration, duration per unit of time), type and site of drug delivery, signal characteristics such as signal shape (or frequency), which if pulsatile can be pulse shape, duration, or frequency, and numerous other characteristics as is known in the art. The stimulation waveform can also be a sinusoidal or other arbitrary shape. Providing stimulation can cause an increase or decrease in the excitation of target tissue, or may cause another type of desired change. Stimulation can refer modulation of any tissue, fluid, process, or level related to a biological process related to the treatment being provided and may include modulation which is excitatory stimulation, inhibitory stimulation, facilitating or deterring of a biological condition as desired, and can refer to increasing the likelihood that biological activity will occur according to certain patterns, certain rates, or in selected manners. The stimulation subsystem can be realized in either a compact module or may be distributed throughout a system.

As used herein "sensing subsystem" generally refers to a subsystem (either as a single module or distributed throughout a system) that provides sensing according to the parameters of a sensing protocol which determines where, when, and how to sense with, for example, one or more of electrical, optical, or chemical sensors. The sensing protocol can be adjusted, based upon time information or the state of the patient, or both.

As used herein "evaluation subsystem" refers to a subsystem that provides evaluation of the sensed data according to the evaluation protocol. The evaluation subsystem can compare features of the sensed data after it has been processed to obtain these measurements. Evaluation can entail comparing these measurements using various treatment criteria and can include using detection protocols designed for detecting events such as medical events. The evaluation subsystem can also compare time information to treatment criteria. The evaluation subsystem is preferably realized as a module within the control subsystem. When sensed data are obtained the control subsystem relies upon an evaluation protocol to determines if, when and how to evaluate the sensed data and determines if stimulation occurs in response to the sensed data. The evaluation protocol can be adjusted based upon patient state, patient responses, level criteria failing to be met and any a combination of these.

As used herein, the term "adjusting" refers to changing or selecting an operation. Adjusting a protocol may include but shall not be limited to selecting or adjusting a value of a parameter of a protocol or a protocol that is to be used, generally by a clinically relevant and significant amount. Adjustment of the treatment program can include, for example, changing or selecting stimulation, sensing, or evaluation algorithm, and can include setting treatment criteria and their values. Adjusting stimulation can include changing the stimulation parameters so as to begin or halt stimulation, and may include the provision of responsive stimulation.

As used herein the term "patient state" generally refers to an actual or predicted state of a patient. Patient state can be derived from time information and/or sensed data information, or patient response data from which the state of the patient can be inferred. In addition to time information, sensed data can be data which is sensed and evaluated to provide a value which is relevant to a patients state (e.g., standing, sitting, sleeping, anxious, experiencing pain) including activity (e.g., eating), whether or not that state or condition is directly relevant to the patient's symptoms (e.g. magnitude of tremor).

As used herein "treatment criterion" generally refers to a criterion to which features of sensed data are compared using the evaluation protocol. The results of this comparison can be used by the stimulation program to determine what type of stimulation takes place; whether stimulation takes place; and whether treatment is determined to be working. For example, failure to meet a treatment criterion may cause stimulation to occur or may cause a change a different stimulation protocol to be selected. Alternatively, success in meeting a treatment criterion may cause stimulation to be halted or may cause the same stimulation protocol to be selected again. A sensed data treatment criterion can be threshold value. A time treatment criterion can be a time value which has been selected to be important to treatment. For example, a time value for waking up can be set to cause the treatment criterion to be evaluated at true when that time occurs, thereby Implementing an "awake protocol" which is to be used when the patient state is calculated to be "awake". A therapy benefit criterion is a type of treatment criterion. The sensing and evaluation protocols can also be changed based upon comparisons using treatment criterion.

As used herein, "therapy benefit criterion" generally refers to a treatment criterion which is used to determine if treatment benefit is increasing, decreasing, or remaining constant, and can be used to determine the success of treatment. The sensing and evaluation protocols can also be changed based upon comparisons using treatment criterion. Therapy benefit criteria are treatment criteria which may be values that can be compared to sensed activity that is directly related to the disorder, such as the detection of abnormal medical events. A therapy benefit criterion can be a trend measure of symptom severity measured over time, where if the trend increases above the therapy benefit treatment criterion then treatment may be evaluated as failing. The therapy benefit treatment criterion can be evaluated by the evaluation subsystem, and will affect operation according to the algorithms of the treatment program. The evaluation of therapy benefit treatment criteria can result not only in this criteria being met or not met, but also can result in scores which determine what to do if the treatment assessed as not to be working. The scores can be computed using the treatment benefit algorithm that is implemented by the evaluation subsystem.

As used herein the term "patient state algorithm" generally describes an algorithm that has "patient state rules" that govern how to define or classify a patient state. Patient state rules can also define one or more operations that occur if the patient state is defined in a particular manner. The patient state algorithm can also adjust the alert protocol implemented by the patient alert module of the control subsystem and can determine what type of alert signals are sent to the patient.

The term "patient," when used herein in connection with user interaction, can be used to refer to a patient, a caregiver (particularly if the patient is disabled), or a physician using the system. Accordingly, then, the term "patient response" refers to a response provided by a patient, caregiver, or doctor. A patient response can be "no response" if no response is provided within a specified time limit. The term "user" may apply to a patient, caregiver, physician, or other individual interacting with a system according to the invention.

The term "alert event" refers to any operation or event for which alerting has been designated to occur.

The term "alert event set" refers to a set of events for which alerts are sent. The alert event set can include: a description of the alert event; a proposed action that are sent for each of the alert events; at least one possible proposed operation which may take place for each of the alert events; and other relevant information, all of which may be part of the alert signal which is sent or which can be later accessed by the patient. Automatically sending an alert and waiting for a response may also be referred to as "notification", and the alert signal is the "notice".

An "operation" can refer to any action performed by a system according to the invention or by a part of such a system, including but not limited to the performance of algorithms (or portions thereof) implementing stimulation, sensing, evaluation, alerting, detection, and other protocols. "Operating" is performing an operation. "Operating protocols" are portions of the treatment program that are used to carry out operations.

An "operating condition" can refer to a detected event, a sensed value, or a data value of a system according to the invention (such as time of day), satisfying a criterion. The criterion can be defined in an alert event set such as (but not limited to), can be a treatment criterion, time criterion, a patient state criterion, or a level criterion. An "operating condition" can be satisfied, for example, simply by an operation occurring or being scheduled to occur, or by a threshold criterion being exceeded by a data value.

The contents of all prior art and scientific references cited in this specification are hereby incorporated by reference as if recited in full herein. The embodiments described herein can be altered, adjusted, or amended without departing from the spirit and scope of the invention, as are reflected in the accompanying claims.

Scientific References.

Brushart T M, Jari R, Verge V, Rohde C, Gordon T. Electrical stimulation restores the specificity of sensory axon regeneration. Exp Neurol. 2005; 194(1): 221-9).

Graham-Jones S, Holt L, Gray J A, Fillenz M. Low-frequency septal stimulation increases tyrosine hydroxylase activity in the hippocampus. Pharmacol Biochem Behav. 1985 October; 23(4): 489-93.

Velisek L, Dreier J P, Stanton P K, Heinemann U, Moshe S L. Lowering of extracellular pH suppresses low-Mg(2+)-induces seizures in combined entorhinal cortex-hippocampal slices. Exp Brain Res. 1994; 101(1): 44-52.

Windels F, Bruet N, Poupard A, Feuerstein C, Bertrand A, Savasta M, Influence of the frequency parameter on extracellular glutamate and gamma-aminobutyric acid in substantia nigra and globus pallidus during electrical stimulation of subthalamic nucleus in rats. J Neurosci Res. 2003 Apr. 15; 72 (2):259-67.

Yavich L, Ylinen A. Spreading depression in the cortex differently modulates dopamine release in rat mesolimbic and nigrostriatal terminal fields. Exp Neurol., 2005.

Ziai w C, Sherman D L, Bhardwaj A, Zhang N, Keyl P M, Mirski M A. Target-specific atecholamine elevation induced by anticonvulsant thalamic deep brain stimulation. Epilepsia. 2005; 46 (6):878-88.

What is claimed is:

1. A system configured for currently providing for medical therapy in fully-automatic, semiautomatic, and user-initiated manners including:
    an implantable medical device configured to provide therapy, the implantable medical device comprising;
    a memory coupled to the processor containing therapy program operations that have been programmably defined with an automatic parameter value which indicates the operation is to be implemented in an automatic, semiautomatic, or user-initiated fashion;
    a processor configured for calculating a patient state value and implementing therapy program operations according to both the automatic parameter value and the patient state value, the processor being further configured to adjust its operation in relation to a patient alert rule based on the characteristics of the alert event and then contingently adjusting the alerting and operating of the device if an external patient programmer does not provide a signal indicative of a patient response within a predetermined interval; and
    an external patient programmer for allowing a patient to input a patient response and for communication with the implanted medical device; and
    an alerting module configured for providing alert signals when selected events occur for which alerting has been defined.

2. A medical monitoring and alerting system including:
    a sensor adapted to detect a medically relevant signal from a patient;
    an implanted device having a signal processor coupled to the sensor for conditioning an analog electrical signal corresponding to the medically relevant signal, thereby producing a conditioned digital signal;
    an alert module configured to provide an alert signal related to an alert event type;
    a programmable memory for storing a plurality of responsive operations associated with different alert types;
    an external patient programmer for presenting alert signals to a patient, communicating with other components of the system and for obtaining patient input;
    at least a first processor coupled to the signal processor, the alert module, the external patient programmer, and the programmable memory, the at least first processor configured to:
        (i) detect the occurrence of an alert event by analyzing the digital signal;
        (ii) determine a type of the alert event based upon a characteristic of the alert event;
        (iii) determine if the type of alert event is one of: (a) a semiautomatic event defined in a semi-automatic event set, or (b) an automatic event defined in an automatic event set as a function of the alert event type; and,
        (iv) operate in the case where the alert event is defined as an automatic event so as to automatically perform an operation associated with the alert event, and operate in the case where the alert event is defined as a semi-automatic alert event by sending an alert request to the alert module, thereby causing the alert module to generate and present to a patient an alert signal based upon a characteristic of the alert event, and then operating as a function of the alert event characteristic in response to patient input provided within a selected interval or to the lack thereof;
    the at least first processor being further configured to adjust its operation in relation to a patient alert rule that contingently adjusts the alerting and operating of the device if the external patient programmer does not provide a signal indicative of a patient response;
    wherein the sensor, the signal processor, the alert module, the programmable memory, the external patient programmer and the at least first processor are disposed so that the medical alert system is designed to alert at least the patient whereby the patient can be ambulatory and the system only defines a patient alert rule in relation to an alert provided to the patient.

3. The system of claim 2 further including at least a second processor to operate in the case where the event is a semi-automatic event to determine whether the input has been received by the external patient programmer within a specified interval after sending the alert request, and if such input has not been received within the specified amount of time, then select and perform one of a plurality of responsive operations, said operation selected according to the characteristic of the alert event.

4. The system of claim 2, wherein the sensor is an implanted electrode and the medically relevant signal reflects a physiological measure.

5. The system of claim 2 wherein the alert events are cardiac related alert events and are classified—as either a serious medically relevant event type or a non-serious medically relevant event type.

6. The system of claim 2 wherein the semi-automatic event set includes alert events having smaller magnitudes than the alert events of the automatic event set.

7. The system of claim 2 wherein selected alert events are programmatically assigned by a user to one of the semi-automatic event set and the automatic event set.

8. The system of claim 2 wherein a patient state value is calculated by a patient state module and includes one of: a patient state value reflecting a current patient state, a patient state value reflecting a change in patient state, and a patient state value reflecting the current patient state for a period of time.

9. The system of claim 8 wherein selected alert events are assigned to the semi-automatic event set and the automatic event set according to the patient state value calculated by a patient state module.

10. The system of claim 8 wherein the type of alert event is adjusted based, on a current patient state value calculated by a patient state module, said value being evaluated using a patient state rule applied to recent patient state values.

11. The system of claim 8 wherein the patient state value is calculated to reflect the likelihood that the patient is awake or asleep or exercising.

12. A medical monitoring and alert system which is configured to concurrently provide for therapy including:
a sensing subsystem including a sensor to sense a medically relevant signal from a patient;
an external patient programmer for obtaining patient input, and allowing the patient to communicate with an implanted device;
a programmable memory for storing a plurality of responsive operations corresponding to a plurality of treatment events, said treatment events being defined as one of: an automatic event defined in an automatic event set; a semi-automatic event defined in a semi-automatic event set; and, a user-initiated event defined in a user-initiated event set;
at least a first processor configured to automatically accomplish at least one operation defined for the automatic event set upon detection of an automatic event signal; semi-automatically accomplish at least one operation defined for the semiautomatic event set upon detection of a semi-automatic event signal, said detection causing the alert module to provide an alert signal according to a patient alert rule related to the characteristic of the event, and then operating responsively to patient input provided within a selected interval or to the lack thereof as a function of the event characteristic; and, accomplish at least one operation defined for the user-initiated event set upon the user providing input defined for the user-initiated event;
the at least first processor being further configured to adjust its operation in relation to a patient alert rule that contingently adjusts the alerting and operating of the device if the external patient programmer does not provide a signal indicative of a patient response within a predetermined interval;
an alert module configured to provide alert signals for selected events;
wherein the alert module, the programmable memory, the external patient programmer, implanted device, and the at least first processor operate to alert at least the patient wherein the alert system only defines a patient alert rule in relation to an alert provided to the patient.

13. The system of claim 12 wherein the sensing subsystem comprises a sensor which provides a sensed signal and which is coupled to an analog-to-digital converter which transforms the sensed signal into a digital signal and wherein the at least first processor is also coupled to the analog to digital converter, the at least first processor configured to:
(i) detect the occurrence of a treatment event which is defined as an alert event by analyzing the digital signal;
(ii) determine the type of the alert event from the defined characteristic;
(iii) determine if the type of alert event is defined for either the semi-automatic event set or the automatic event set; and,
(iv) operate in the case where the event is defined in the semiautomatic event set by operating to select an alert signal type according to both the type of alert event and a patient state value, and send a corresponding alert request to the alert module upon detecting the occurrence of the alert event, thereby causing the alert module to generate an alert signal according to the alert signal type; and to operate while awaiting a patient input response to the alert signal based upon at least one patient input response rule and one send alert rule of an alert rule set; and,
(v) operate in the case where the event is defined by the automatic event set by automatically performing an associated operation.

14. The system of claim 13 further including a patient state module for calculating a patient state value.

15. The system of claim 14 wherein the patient state value includes information regarding whether a feature of the sensed data is outside of a selected range.

16. The system of claim 13, further including a treatment subsystem which provides at least one of electrical and drug therapy.

17. The system of claim 12 wherein the alert signal is provided to the user using at least one of: implanted alerting circuitry; and, alerting circuitry of an external patient programmer.

18. The system of claim 12 wherein the alert signal is related to an alert event related to a metabolic disorder.

19. The system of claim 12 wherein the alert signal is an alert event related to a diabetic disorder.

20. The system of claim 12 wherein the alert signal is an alert event related to a neurological disorder.

21. The system of claim 12 wherein the alert signal is an alert event related to a cardiac disorder.

22. The system of claim 21 wherein the cardiac disorder involves ischemia.

23. The system of claim 12 wherein the user-initiated event is defined by patient input and includes one of the taking of medication, adjustment of drug delivery, and exercise.

24. The system of claim 12 wherein the treatment is provided to a target which is at least one of the following: the brain; a cardiovascular target; a vagus nerve; a cranial nerve; a target which modulates the parasympathetic nervous system; a target which modulates the sympathetic nervous system.

25. The system of claim 12 wherein at least one of semi-automatic and fully-automatic events are defined as events which are used by the processor to implement a control-law which regulates the provision of therapy.

* * * * *